United States Patent
Gradilone et al.

(10) Patent No.: US 11,666,569 B2
(45) Date of Patent: Jun. 6, 2023

(54) TREATMENT OF POLYCYSTIC DISEASES WITH AN HDAC6 INHIBITOR

(71) Applicant: MAYO FOUNDATION FOR MEDICAL EDUCATION AND RESEARCH, Rochester, MN (US)

(72) Inventors: Sergio A. Gradilone, Rochester, MN (US); Nicholas F. LaRusso, Rochester, MN (US)

(73) Assignee: NATIONAL INSTITUTES OF HEALTH (NIH), U.S. DEPT. OF HEALTH AND HUMAN SERVICES (DHHS) U.S. GOVERNMENT, Bethesda, MD (US)

( * ) Notice: Subject to any disclaimer, the term of this patent is extended or adjusted under 35 U.S.C. 154(b) by 0 days.

(21) Appl. No.: 16/874,251

(22) Filed: May 14, 2020

(65) Prior Publication Data

US 2021/0161891 A1    Jun. 3, 2021

Related U.S. Application Data

(63) Continuation of application No. 14/523,319, filed on Oct. 24, 2014, now Pat. No. 10,660,890.

(60) Provisional application No. 61/895,223, filed on Oct. 24, 2013.

(51) Int. Cl.
*A61K 31/505* (2006.01)

(52) U.S. Cl.
CPC .................. *A61K 31/505* (2013.01)

(58) Field of Classification Search
CPC .................. A61K 31/505
See application file for complete search history.

(56) References Cited

U.S. PATENT DOCUMENTS

| | | | |
|---|---|---|---|
| 3,549,633 A | 12/1970 | Grabowski et al. | |
| 6,777,217 B1 | 8/2004 | Schreiber et al. | |
| 7,244,853 B2 | 7/2007 | Schreiber et al. | |
| 7,250,504 B2 | 7/2007 | Grozinger et al. | |
| 7,994,362 B2 | 8/2011 | Schreiber et al. | |
| 8,148,526 B1 | 4/2012 | van Duzer et al. | |
| 8,394,810 B2 | 3/2013 | van Duzer et al. | |
| 8,609,678 B2 | 12/2013 | van Duzer et al. | |
| 8,614,223 B2 | 12/2013 | van Duzer et al. | |
| 2004/0266769 A1 | 12/2004 | Bressi et al. | |
| 2005/0119305 A1 | 6/2005 | Naka et al. | |
| 2006/0239909 A1 | 10/2006 | Anderson et al. | |
| 2007/0093413 A1 | 4/2007 | Schreiber et al. | |
| 2007/0149495 A1 | 6/2007 | Bressi et al. | |
| 2008/0207590 A1 | 8/2008 | Deziel et al. | |
| 2009/0023786 A1 | 1/2009 | Miller et al. | |
| 2009/0209590 A1 | 8/2009 | Mazitschek et al. | |
| 2009/0305384 A1 | 12/2009 | Grozinger et al. | |
| 2009/0312363 A1 | 12/2009 | Bradner et al. | |
| 2010/0137196 A1 | 6/2010 | Schreiber et al. | |
| 2010/0152254 A1 | 6/2010 | Bialer et al. | |
| 2010/0168463 A1 | 7/2010 | Hirata et al. | |
| 2010/0330197 A1 | 12/2010 | Higashiguchi et al. | |
| 2011/0218154 A1 | 9/2011 | Schreiber et al. | |
| 2012/0121502 A1 | 5/2012 | van Duzer et al. | |
| 2013/0225543 A1 | 8/2013 | Jones et al. | |
| 2014/0011767 A1 | 1/2014 | Yang et al. | |
| 2014/0142104 A1 | 5/2014 | van Duzer et al. | |
| 2014/0142117 A1 | 5/2014 | van Duzer et al. | |
| 2014/0357512 A1 | 12/2014 | Jones et al. | |
| 2015/0045380 A1 | 2/2015 | van Duzer et al. | |
| 2015/0239869 A1 | 2/2015 | Mazitschek et al. | |
| 2015/0099744 A1 | 4/2015 | Yang et al. | |
| 2015/0105358 A1 | 4/2015 | Quayle et al. | |
| 2015/0105383 A1 | 4/2015 | Quayle et al. | |
| 2015/0105384 A1 | 4/2015 | Jones et al. | |
| 2015/0105409 A1 | 4/2015 | Quayle et al. | |
| 2015/0150871 A1 | 6/2015 | Quayle et al. | |
| 2015/0176076 A1 | 6/2015 | Yang et al. | |
| 2016/0030458 A1 | 2/2016 | Jones et al. | |

FOREIGN PATENT DOCUMENTS

| | | |
|---|---|---|
| EP | 2 524 918 A1 | 11/2012 |
| WO | 2001/070675 A2 | 9/2001 |
| WO | 2002/074298 A1 | 9/2002 |

(Continued)

OTHER PUBLICATIONS

Pugacheva EN, Jablonski SA, Hartman TR, Henske EP, and Golemis EA (2007) HEF1-dependent Aurora A activation induces disassembly of the primary cilium. Cell 129:1351-1363. (Year: 2007).*
Cao Y, Semanchik N, Lee SH, Somlo S, Barbano PE, Coifman R, and Sun Z (2009) Chemical modifier screen identifies HDAC inhibitors as suppressors of PKD models. Proc Natl Acad Sci USA 106:21819-21824. (Year: 2009).*
Pang et al. (JPET Nov. 2010 vol. 335 No. 2 266-272) (Year: 2010).*
Butler et al. (2000) "Suberoylanilide Hydroxamic Acid, an Inhibitor of Histone Deactetylase, Suppresses the Growth of Prostate Cancer Cells in Vitro and in Vivo," Cancer Research. 60:5165-5170.
Costello et al. (Dec. 2012) "Evidence for Changes in RREB-1, ZIP3, and Zinc in the Early Development of Pancreatic Adenocarcinoma," J. Gastrointest. Canc. 43:570-578.
Dokmanovic et al. (2007) "Histone Deacetylase Inhibitors: Overview and Perspectives," Mol. Cancer Res. 5(10):981-989.

(Continued)

*Primary Examiner* — Jeffrey S Lundgren
*Assistant Examiner* — William Y Lee
(74) *Attorney, Agent, or Firm* — Brian C. Trinque; Lathrop GPM LLP

(57) ABSTRACT

An HDAC6-specific inhibitor (i.e., a compound of Formula I or II) is shown to reduce the pathogenesis associated with polycystic disease. Administration of an HDAC6-specific inhibitor attenuated many of the symptoms characteristic of polycystic liver disease including cyst formation, cyst growth and cholangiocyte proliferation. Treatment with a HDAC6-specific inhibitor also increased the amount of bile duct acetylated tubulin and β-catenin phosphorylation and/or acetylation while reducing bile duct β-catenin synthesis. These results demonstrate that HDAC6 is overexpressed in cystic cholangiocytes and that its pharmacological inhibition reduces cholangiocyte proliferation and cyst growth.

17 Claims, 10 Drawing Sheets

Specification includes a Sequence Listing.

(56) References Cited

FOREIGN PATENT DOCUMENTS

| | | |
|---|---|---|
| WO | 2003/037869 A1 | 5/2003 |
| WO | 2003/076401 A1 | 9/2003 |
| WO | 2003/076430 A1 | 9/2003 |
| WO | 2004/052869 A1 | 6/2004 |
| WO | 2005/012261 A1 | 2/2005 |
| WO | 2005/028447 A1 | 3/2005 |
| WO | 2005/030705 A1 | 4/2005 |
| WO | 2006/102557 A2 | 9/2006 |
| WO | 2006/123121 A1 | 11/2006 |
| WO | 2007/022638 A1 | 3/2007 |
| WO | 2007/091703 A2 | 8/2007 |
| WO | 2007/130429 A2 | 11/2007 |
| WO | 2007/144341 A1 | 12/2007 |
| WO | 2008/003801 A1 | 1/2008 |
| WO | 2008/033746 A2 | 3/2008 |
| WO | 2008/055068 A2 | 5/2008 |
| WO | 2008/091349 A1 | 7/2008 |
| WO | 2009/137462 A1 | 11/2009 |
| WO | 2009/137503 A1 | 11/2009 |
| WO | 2010/009155 A2 | 1/2010 |
| WO | 2010/011296 A2 | 1/2010 |
| WO | 2010/014611 A1 | 2/2010 |
| WO | 2010/080996 A1 | 7/2010 |
| WO | 2010/131922 A2 | 11/2010 |
| WO | 2011/006040 A2 | 1/2011 |
| WO | 2011/011186 A1 | 1/2011 |
| WO | 2011/019393 A2 | 2/2011 |
| WO | 2011/084991 A2 | 7/2011 |
| WO | 2011/091213 A2 | 7/2011 |
| WO | 2011/146855 A1 | 11/2011 |
| WO | WO 2012/018499 A2 | 2/2012 |
| WO | 2012/068109 A2 | 5/2012 |
| WO | 2013/013113 A2 | 1/2013 |
| WO | 2013013113 A2 | 1/2013 |

OTHER PUBLICATIONS

Giannini et al. (Jul. 2012) "Histone Deacetylase Inhibitors in the Treatment of Cancer: Overview and Perspectives," Future Med. Chem. 4(11):1439-1460.
Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.
Kozikowski et al. (2008) "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6," Journal of Medicinal Chemistry. 51:4370-4373.
Lane et al. (2009) "Histone Deacetylase Inhibitors in Cancer Therapy," J. Clin. Oncol. 27:5459-5468.
Loudni et al. (2007) "Design, synthesis and biological evaluation of 1,4-benzodiazepine-2, 5-dione-based HDAC inhibitors," Bioorganic and Medicinal Chemistry Letters. 17:4819-4823.
Mazitschek et al. (2008) "Development of a Fluorescence Polarization Based Assay for Histone Deacetylase Ligand Discovery," Bioorganic and Medicinal Chemistry Letters. 18(9):2809-2812.
Miller et al. (1998) "Paclitaxel as the Initial Treatment of Multiple Myeloma: An Eastern Cooperative Oncology Group Study (E1A93)," Am. J. Clin. Oncol. 21(6):553-556.
Perez (1998) "Paclitaxel in Breast Cancer," The Oncologist. 3:373-389.
Ropero et al. (2007) "The Role of Histone Deacetylases (HDACs) in Human Cancer," Molecular Oncology. 1:19-25.
Smil et al. (2009) "Novel HDAC6 Isoform Selective Chiral Small Molecule Histone Deacetylase Inhibitors," Bioorganic and Medicinal Chemistry Letters. 19:688-692.
Sporn et al. (2000) "Chemoprevention of Cancer," Carcinogenesis. 21(3):525-530.
Thoppil et al. (Sep. 2011) "Terpenoids as Potential Chemopreventive and Therapeutic Agents in Liver Cancer," World J. Hepatol. 3(9):228-249.
International Search Report with Written Opinion corresponding to International Patent Application No. PCT/US2011/021982, dated Oct. 10, 2011.
Search Opinion corresponding to European Patent Application No. 11735212, dated Jun. 26, 2014.
Written Opinion corresponding to Singapore Patent Application No. Application No. 201205393-0, dated Nov. 15, 2013.
Angibaud et al. (2005) "Discovery of Pyrimidyl-5-hydroxamic acids as New Potent Histone Deacetylase Inhibitors," European Journal of Medicinal Chemistry. 40(6):597-606.
Brana et al. (2002) "Synthesis and biological evaluation of novel 2-(1H-imidazol-4-yl)cyclopropane carboxylic acids: key intermediates for H3 histamine receptor ligands," BioOrganic & Medicinal Chemistry Letter. 12(24):3561-3563.
Broxterman et al. (1992) "Synthesis of (optically active) sulfur-containing trifunctional amino acids by radical addition to (optically active) unsaturated amino acids," The Journal of Organic Chemistry. 57(23):6286-6294.
Carey et al. (2006) "Histone deacetylase inhibitors: gathering pace," Current Opinion in Pharmacology. 6:369-375.
Chuang et al. (2009) "Multiple roles of HDAC inhibition in neurodegenerative conditions," Trends in Neurosciences. 32(11):591-601.
Dallavalle et al. (2012) "Development and therapeutic impact of HDAC6-selective inhibitors," Biochemical Pharmacology. 84:756-765.
Elaut et al. (2007) "The Pharmaceutical Potential of Histone Deacetylase Inhibitors," Current Pharmaceutical Design. 13:2584-2620.
Foks et al. (1972) "Investigations on Pyrazine Derivatives Part II. Synthesis and Tuberculostatic Action of Some 6Alkylaminopyrazine-2-carboxylic acids," Dissertationes Pharmaceuticae and Pharmacologicae 24:(6)577-583.
Foks et al. (1974) "Studies on Pyrazine Derivatives," Pol. J. Pharmacol. Pharm. 26:537-543.
Neidle, Stephen: Ed. (2008) Cancer Drug Design and Discovery. Elsevier/Academic Press. pp. 427-431.
Pellicciar et al. (1996) "Synthesis and Pharmacological Characterization of All Sixteen Stereoisomers of 2-(2'-Carboxy-3'-phenylcyclopropyl)glycine. Focus on (2S,1'S,2'S,3'R)-2-(2'-Carboxy-3'-phenylcyclopropyl)glycine, a Novel and Selective Group II Metabotropic Glutamate Receptors Antagonist," Journal of Medicinal Chemistry 39(11):2259-2269.
Rajak et al. (2011) "2,5-Disubstituted-1,3,4-oxadiazoles/thiadiazole as Surface Recognition Moiety: Design and Synthesis of Novel Hydroxamic acid Based Histone Deacetylase Inhibitors," Bioorganic & Medicinal Chemistry Letters. 21(19):5735-5738.
Nalbrick et al.(1968) "A general method for synthesizing optically active 1,3-disubstituted allene hydrocarbons," The Journal of the American Chemical Society 90(11):2895-2901.
Warner et al. (1992) "Electron demand in the transition state of the cyclopropylidene to allene ring opening," The Journal of Organic Chemistry. 57(23):6294-6300.
International Preliminary Report on Patentability corresponding to International Patent Application No. PCT/US2011/060791, dated Jul. 22, 2014.
International Search Report with Written Opinion corresponding to International Patent Application No. PCT/US2011/060791, dated Mar. 5, 2014.
Supplementary European Search Report corresponding to European Application No. 11840803.8, dated Mar. 5, 2014.
Jochems et al. (Aug. 19, 2013) "Antidepressant-Like Properties of Novel HDAC6-Selective Inhibitors with Improved Brain Bioavailability," Neuropsychopharmacol. 39(2):389-400.
Liu et al. (Nov. 13, 2012) "HDAC6 Regulates Epidermal Growth Factor Receptor (EGFR) Endocytic Trafficking and Degradation in Renal Epithelial Cells," PLoS One. 7(11):e49418. pp. 1-12.
Li (2011) "Epigenetics and autosomal dominant polycystic kidney disease." Biochimica et Biophysica Acta (BBA)—Molecular Basis of Disease. 1812(10):1213-1218.
International Search Report with Written Opinion corresponding to International Patent Application No. PCT/US2014/062175, dated Jan. 22, 2015.

(56) References Cited

OTHER PUBLICATIONS

Habringer et al., "HDAC6 is overexpressed in cystic cholangiocytes and its inhibition reduces cystogenesis", *Hepatology* 56(4 Suppl):335A, Article 290 (2012).

* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcagcgcagt cttatggatg                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcggtggatg gagaaataga                                                  20
```

TREATMENT OF POLYCYSTIC DISEASES WITH AN HDAC6 INHIBITOR

RELATED APPLICATIONS

This application claims priority to and the benefit of U.S. Provisional Application No. 61/895,223, filed Oct. 24, 2013, which is hereby incorporated by reference in its entirety.

GOVERNMENT FUNDING

This invention was made with government support under P30DK084567, R21CA166635 and R01 DK24031 awarded by the National Institutes of Health (NIH). The government has certain rights in the invention.

TECHNICAL FIELD

This disclosure reports on the administration of HDAC6 inhibitors for the treatment of polycystic diseases.

BACKGROUND

Post-translational modification of proteins through acetylation and deacetylation of lysine residues plays a critical role in regulating a variety of cellular functions, including the control of cell shape, differentiation and proliferation. Histone deacetylases (HDACs) are zinc-binding hydrolases that catalyze the deacetylation of lysine residues on histones as well as non-histone proteins (Haberland et al Nature Rev. Genet. 2009, 10, 32-42). Eleven Zn binding human HDACs have been identified (Taunton et al. Science 1996, 272, 408-411; Yang et al. J. Biol. Chem. 1997, 272, 28001-28007; Grozinger et al. Proc. Natl. Acad. Sd. U.S.A. 1999, 96, 4868-4873; Kao et al. Genes Dev. 2000, 14, 55-66. Hu et al J. Biol. Chem. 2000, 275, 15254-15264; Zhou et al. Proc. Natl. Acad. Sci U.S.A. 2001, 98, 10572-10577; Venter et al. Science 2001, 291, 1304-1351). These members are classified into four families: Class I (HDAC1, 2 and 3), Class IIa (HDAC4, 5, 7 and 9), Class IIb (HDAC6 and 10) and Class IV (HDAC11).

Class I HDACs (HDACs 1, 2 and 3) modulate gene expression through deacetylation of the N-acetyl-lysine residues of histone proteins and other transcriptional regulators in the nucleus of the cell (Hassig et al. Curr. Opin. Chem. Biol. 1997, 1, 300-308).

HDAC6, a class IIb HDAC, is unique amongst the zinc dependent HDACs in humans. Located in the cytoplasm, HDAC6 has two catalytic domains and an ubiquitin binding domain in its C terminal region. The substrates of HDAC 6 include tubulin, peroxiredoxin, cortactin and heat shock protein 90 (hsp90) but not histones. HDAC6 plays a key role in microtubule dynamics including cell migration and cell-cell interactions and it is required for aggresome formation with ubiquitinated proteins.

Provided herein are small molecule inhibitors of HDAC6, pharmaceutical compositions thereof, and methods of using these compounds to treat polycystic diseases.

SUMMARY OF THE INVENTION

This disclosure provides for methods of treating polycystic disease comprising administering to a subject with polycystic disease a therapeutically effective amount of a histone deacetylase 6 (HDAC6) specific inhibitor compound of Formula I:

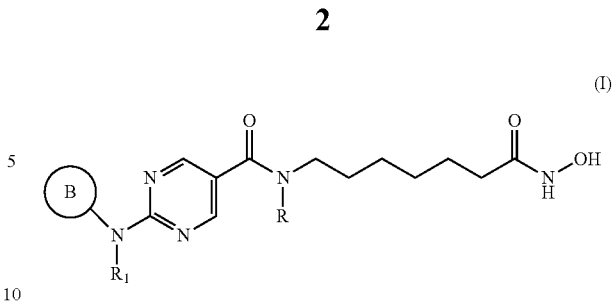

(I)

or a pharmaceutically acceptable salt thereof,
wherein ring B is aryl or heteroaryl, $R_1$ is an aryl or heteroaryl, each of which may be optionally substituted by OH, halo, or $C_{1-6}$-alkyl, and R is H or $C_{1-6}$-alkyl, and wherein the amount of the histone deacetylase 6 (HDAC6) specific inhibitor compound of Formula I is effective at reducing cyst growth in the subject.

This disclosure also provides for methods of treating polycystic disease comprising administering to a subject with polycystic disease a therapeutically effective amount of a histone deacetylase 6 (HDAC6) specific inhibitor compound of Formula II:

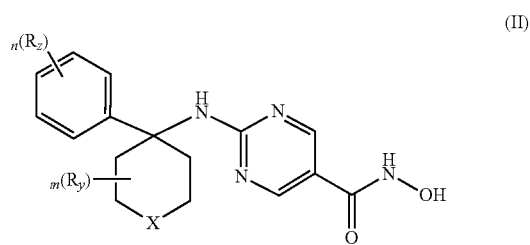

(II)

or a pharmaceutically acceptable salt thereof,
wherein,
X is C or O;
$R_y$ is independently, at each occurrence, selected from the group consisting of $C_{1-6}$-alkyl, $C_{1-6}$-alkoxy, halo, —$C_{1-6}$ haloalkyl, —$C_{1-6}$ dihaloalkyl, —$C_{1-6}$ trihaloalkyl, —OH, —$N(R^1)_2$, —C(O)R', —$CO_2R^1$, and —$C(O)N(R^1)_2$;
or:
two $R_y$ groups on the same or adjacent carbon atoms are taken together to form a $C_{3-8}$-cycloalkyl or $C_{3-7}$-heterocycloalkyl ring, each of which may be fused or isolated;
$R_z$ is independently, at each occurrence, selected from the group consisting of $C_{1-6}$-alkyl, $C_{1-6}$-alkoxy, halo, —$C_{1-6}$ haloalkyl, —$C_{1-6}$ dihaloalkyl, —$C_{1-6}$ trihaloalkyl, —OH, —$N(R^2)_2$, —C(O)R², —$CO_2R^2$, —$C(O)N(R^2)_2$,
each $R^1$ is independently, at each occurrence, selected from the group consisting of H, $C_{1-6}$-alkyl, $C_{3-8}$-cycloalkyl, $C_{3-7}$-heterocycloalkyl, aryl, heteroaryl, $C_{1-6}$-alkyl-cycloalkyl, $C_{1-6}$-alkyl-heterocycloalkyl, $C_{1-6}$-alkyl-aryl, and $C_{1-6}$-alkyl-heteroaryl;
each $R^2$ is independently, at each occurrence, selected from the group consisting of H or $C_{1-6}$-alkyl;
m is 0, 1, 2, or 3; and
n is 0, 1, 2, or 3.
and wherein the amount of the histone deacetylase 6 (HDAC6) specific inhibitor compound of Formula II is effective at reducing cyst growth in the subject.

In certain embodiments, the histone deacetylase 6 (HDAC6) specific inhibitor compound prevents the formation of cysts in the subject.

In certain embodiments, the cysts can be located in the liver and/or kidney.

In certain embodiments, the subject has a mutation in at least one of the PRKCSH (Protein Kinase C Substrate 80K-H) and Sec63 genes.

In certain embodiments, the polycystic disease is renal cystic disease.

In certain embodiments, the polycystic disease is the polycystic kidney disease.

In certain embodiments, the polycystic disease is an autosomal dominant polycystic kidney disease (ADPKD). The subject can have a mutation in at least one of the Pkd1 and Pkd2 genes.

In certain embodiments, the polycystic disease is an autosomal recessive polycystic kidney disease (ARPKD). The subject can have a mutation in the Pkhd1 gene.

In certain embodiments, the amount of the HDAC6 specific inhibitor compound is effective at inhibiting cholangiocyte proliferation and/or bile duct β-catenin synthesis and/or promoting bile duct β-catenin phosphorylation and/or acetylation.

In certain embodiments, the amount of the HDAC6 specific inhibitor compound is effective at increasing the amount of bile duct acetylated tubulin and/or decreasing bile duct β-catenin synthesis.

In certain embodiments, the histone deacetylase 6 (HDAC6) specific inhibitor compound of Formula I is Compound A-1 having the structure:

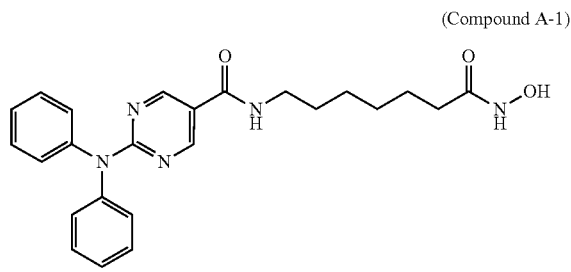 [SMILES: O=C(CCCCCCNC(=O)c1cnc(N(c2ccccc2)c2ccccc2)nc1)NO]

(Compound A-1)

or a pharmaceutically acceptable salt thereof, or Compound B-1 having the structure:

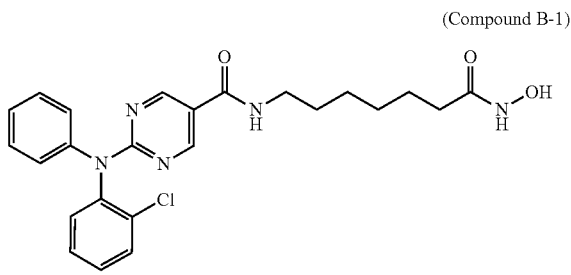 [SMILES: O=C(CCCCCCNC(=O)c1cnc(N(c2ccccc2)c2ccccc2Cl)nc1)NO]

(Compound B-1)

or a pharmaceutically acceptable salt thereof.

In certain embodiments, the amount of the histone deacetylase 6 (HDAC6) specific inhibitor compounds A-1 and B-1 are effective at reducing cyst growth in a subject.

In certain embodiments, the amount of the histone deacetylase 6 (HDAC6) specific inhibitor compounds A-1 and B-1 are effective at inhibiting cholangiocyte proliferation.

In certain embodiments, the histone deacetylase 6 (HDAC6) specific inhibitor compound of Formula II is Compound C-2 having the structure:

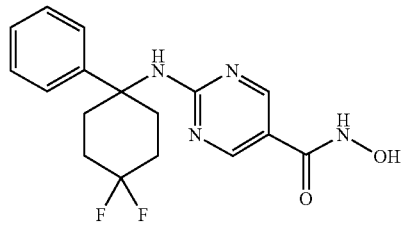

(Compound C-2)

or a pharmaceutically acceptable salt thereof.

In certain embodiments, the amount of the histone deacetylase 6 (HDAC6) specific inhibitor compound C-2 is effective at reducing cyst growth in a subject.

In certain embodiments, the amount of the histone deacetylase 6 (HDAC6) specific inhibitor compound C-2 is effective at inhibiting cholangiocyte proliferation.

In certain embodiments, the disclosure teaches a kit comprising a therapeutically effective amount of HDAC6 specific inhibitor compounds of Formula I or II and instructions for use in treating a polycystic disease.

BRIEF DESCRIPTION OF THE DRAWINGS

FIG. 1A: PCR analysis showing HDAC6 mRNA expression in both normal (NRC) and PCK rats cholangiocytes. FIG. 1B: Representative Western blot for HDAC6 and acetylated-α-tubulin expression in NRC and PCK rat cholangiocytes and densitometric analysis of the western blot results. (* p<0.05, 6 n=3 for control, n=4 for PCK). FIG. 1C, Immunofluorescence confocal microscopy of liver cysts in PCK rats (n=5), human ADPKD (n=3) and ARPKD (n=3) livers and respective controls (n=5 and 3 for rats and humans). HDAC6 is green, CK19 is red, and nuclei are blue (DAPI).

FIG. 2A shows the level of PCK rat cholangiocytes proliferation over time in the presence of different doses of tubastatin-A. (*p<0.05). FIG. 2B shows tubastatin-A and tubacin decrease the proliferation of PCK rat cholangiocytes over a 3 day time period. (*p<0.05). FIG. 2C depicts representative images of biliary cysts freshly isolated from PCK rats. The cysts were embedded in rat tail collagen matrix and treated with two different HDAC6 specific inhibitors, tubastatin-A and tubacin. FIG. 2D shows a quantitative analysis of cyst growth over time and that both inhibitors (n=12 for 10 uM tubastatinA, n=4 for 2 uM tubacin, n=16 for untreated controls. Magnification 40×. *p<0.05) significantly reduce cyst growth.

FIG. 3A depicts representative images of western blots (n=3) demonstrating that treatment with the HDAC6 inhibitors increases acetylated α-tubulin levels while decreasing β-catenin, cyclin D1 and c-myc. The acetylation levels of histone-3 remained unaffected. Actin was used as a loading control. FIG. 3B depicts representative images of Western blots (n=3) showing HDAC6 inhibitors increase the amount of phospho- and acetyl-β-catenin compared to untreated cells using total-β- catenin as loading control. FIG. 3C depicts Western blots and RT-PCR analysis showing a decrease in β-catenin protein expression over time after treatment with 2 uM tubacin, while β-catenin mRNA remained stable. (* p<0.05).

FIG. 4A depicts proliferation assays on normal (NRC) and cystic cholangiocytes (PCK) incubated in the presence of different doses of Compound A-1. FIG. 4B depicts representative liver and kidney sections stained with picrosirius red from PCK rats treated with vehicle (n=8) or Compound A-1 (n=8). Bar=2500 μm. FIG. 4C, quantification analysis of cystic area expressed as percentage of total parenchyma area. *p<0.05.

DETAILED DESCRIPTION OF THE INVENTION

Definitions

Figure 1A:
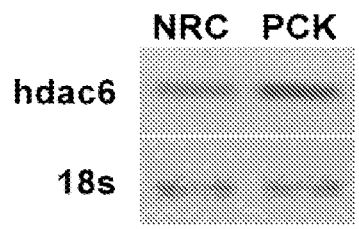
FIGS. 1A-1C shows an analysis of HDAC6 expression in cystic cholangiocytes.

Listed below are definitions of various terms used to describe this invention. These definitions apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. Examples of $C_1$-$C_6$ alkyl moieties include, but are not limited to, methyl, ethyl, propyl, isopropyl, n-butyl, tert-butyl, neopentyl, n-hexyl moieties; and examples of $C_1$-$C_8$ alkyl moieties include, but are not limited to, methyl, ethyl, propyl, isopropyl, n-butyl, tert-butyl, neopentyl, n-hexyl, heptyl, and octyl moieties.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl and the like. In some embodiments, aryl groups have 6 carbon atoms. In some embodiments, aryl groups have from six to ten carbon atoms. In some embodiments, aryl groups have from six to sixteen carbon atoms.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like.

The term "halo" refers to a halogen, such as fluorine, chlorine, bromine, and iodine.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the terms "treating," "treatment" and the like are used herein to mean obtaining a desired pharmacologic and/or physiologic effect that at least alleviates or abates a polycystic disease. The effect may be prophylactic in terms of completely or partially preventing a polycystic disease or sign or symptom thereof, and/or may be therapeutic in terms of a partial or complete cure for a polycystic disease and/or adverse effect attributable to the polycystic disease. "Treating" also covers any treatment of a polycystic disease in a mammal, and includes: (a) preventing a polycystic disease from occurring in a subject that may be predisposed to a polycystic disease, but has not yet been diagnosed as having it; (b) inhibiting a polycystic disease, i.e., arresting its development; or (c) relieving or ameliorating the polycystic disease, e.g., cause regression of the polycystic disease. As used herein, to "treat" includes systemic amelioration of the symptoms associated with the pathology and/or a delay in onset of symptoms. Clinical and subclinical evidence of "treatment" will vary with the pathology, the individual and the treatment.

In certain embodiments, the terms "treating" or "treatment" can refer to reducing cholangiocyte proliferation, bile duct β-catenin synthesis or bile duct β-catenin phosphorylation and/or acetylation. In other embodiments, the terms "treating" or "treatment" can refer to increasing the amount of bile duct acetylated tubulin and/or bile duct β-catenin synthesis.

As used herein, the term "polycystic disease" is a disease characterized by the formation of cysts. Examples of polycystic disease includes, but is not limited to, renal cystic disease such as polycystic kidney disease (PKD), polycystic liver disease (PLD), polycystic ovary syndrome (PCOS), pancreatic cysts, or combinations thereof.

Polycystic diseases can include cholangiopathies, a group of liver diseases in which cholangiocytes, the epithelia lining the biliary tree are the target cells. "Cholangiopathies" include, but are not limited to, primary biliary cirrhosis, primary sclerosing cholangitis, AIDS cholangiopathy, disappearing bile duct syndromes, Alagille's syndrome, cystic fibrosis, and biliary atresia (see Tietz P S, Larusso N F (2006). "Cholangiocyte biology". Current Opinion in Gastroenterology 22 (3): 279-87).

Polycystic disease can also include liver diseases where the liver or liver function is compromised by dysfunction and/or imbalance in salt and/or water homeostasis or balance, such as diseases, disease states, and disorders that include the presence of liver cysts. Illustrative liver diseases include, but are not limited to chronic hepatic liver fibrosis, PLD accompanying PKD, nephronophthisis (NPHP), Meckel-Gruber Syndrome, Bardet-Biedl Syndrome, and the like.

A clinical symptom of polycystic liver disease that can be treated by an HDAC6 inhibitor compound of Formula I or II includes, but is not limited to, hepatomegaly, multiple macrocysts within the liver, in cases of isolated polycystic liver disease, or liver and kidney, in cases of autosomal dominant polycystic kidney disease which can cause abdominal distension, a shortness of breath, early postprandial fullness, abdominal discomfort, and back discomfort. Other clinical symptoms of severe polycystic liver disease include portal hypertension, variceal bleeding, jaundice, ascites and, in rare cases, cystic carcinoma as well as "pseudo" Budd-Chiari syndrome resulting from a blockage of venous drainage from the liver.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 16th Edition, 1980 and 17th Edition, 1985, both published by Mack Publishing Company, Easton, Pa., page 1418 and Journal of Pharmaceutical Science, 66, 2 (1977), each of which is incorporated herein by reference in its entirety.

Compounds of the Invention

In some embodiments, the HDAC6 specific inhibitor is a compound of Formula I:

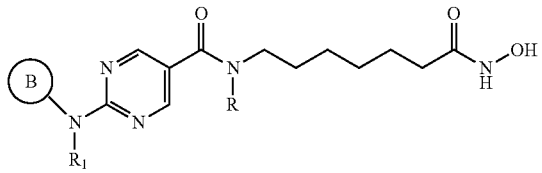

(I)

or a pharmaceutically acceptable salt thereof,
wherein,
ring B is aryl or heteroaryl;
$R_1$ is an aryl or heteroaryl, each of which may be optionally substituted by OH, halo, or alkyl;
and
R is H or alkyl.

Representative compounds of Formula I are shown in TABLE I below and include, but are not limited to:

TABLE I

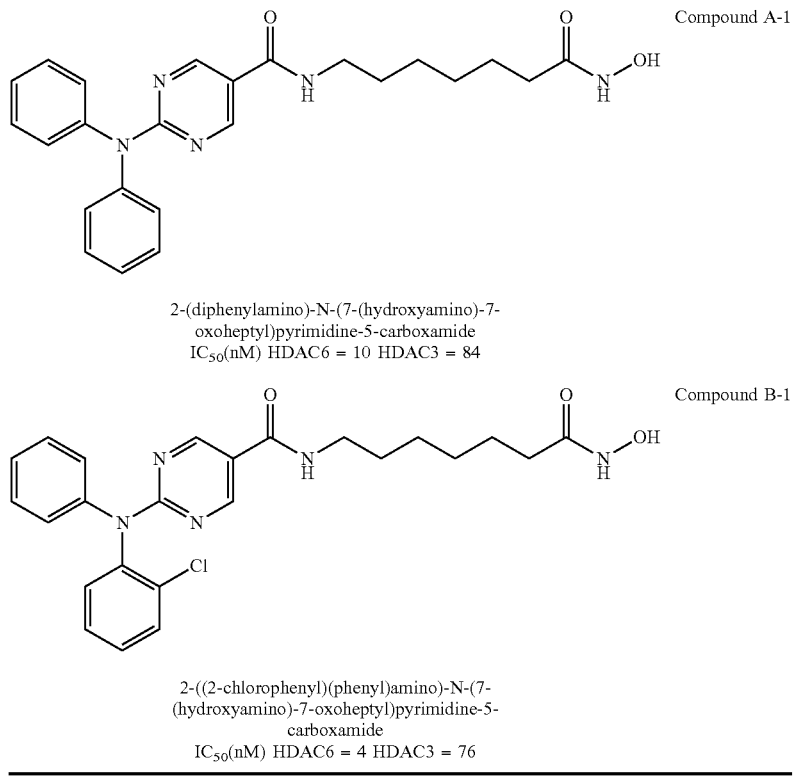

or pharmaceutically acceptable salts thereof.

The preparation and properties of selective HDAC6 inhibitors according to Formula I are provided in International patent Application No. PCT/US2011/021982, the entire contents of which is incorporated herein by reference.

In other embodiments, the HDAC6 specific inhibitor is a compound of Formula II:

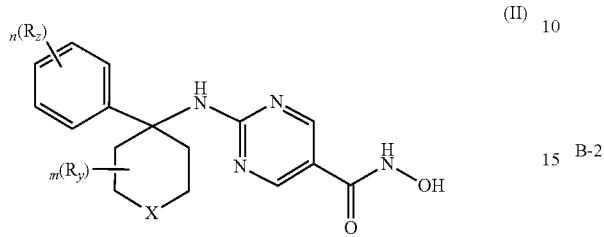

(II)

or a pharmaceutically acceptable salt thereof, wherein,

X is C or O;

$R_y$ is independently, at each occurrence, selected from the group consisting of $C_{1-6}$-alkyl, $C_{1-6}$-alkoxy, halo, —$C_{1-6}$ haloalkyl, —$C_{1-6}$ dihaloalkyl, —$C_{1-6}$ trihaloalkyl, —OH, —$N(R^1)_2$, —$C(O)R'$, —$CO_2R^1$, and —$C(O)N(R^1)_2$;

or:

two $R_y$ groups on the same or adjacent carbon atoms are taken together to form a $C_{3-8}$-cycloalkyl or $C_{3-7}$-heterocycloalkyl ring, each of which may be fused or isolated;

$R_z$ is independently, at each occurrence, selected from the group consisting of $C_{1-6}$-alkyl, $C_{1-6}$-alkoxy, halo, —$C_{1-6}$ haloalkyl, —$C_{1-6}$ dihaloalkyl, —$C_{1-6}$ trihaloalkyl, —OH, —$N(R^2)_2$, —$C(O)R^2$, —$CO_2R^2$, —$C(O)N(R^2)_2$, each $R^1$ is independently, at each occurrence, selected from the group consisting of H, $C_{1-6}$-alkyl, $C_{3-8}$-cycloalkyl, $C_{3-7}$-heterocycloalkyl, aryl, heteroaryl, $C_{1-6}$-alkyl-cycloalkyl, $C_{1-6}$-alkyl-heterocycloalkyl, $C_{1-6}$-alkyl-aryl, and $C_{1-6}$-alkyl-heteroaryl;

each $R^2$ is independently, at each occurrence, selected from the group consisting of H or $C_{1-6}$-alkyl;

m is 0, 1, 2, or 3; and n is 0, 1, 2, or 3.

In an embodiment of the compounds of Formula II, n is 1 or 2 and $R_z$ is halo.

In another embodiment of the compounds of Formula II, X is C and m is 1 or 2. In a preferred embodiment, X is C, m is 1 or 2, and $R_y$ is halo or $C_{1-6}$-alkoxy. In another embodiment, two $R_y$ groups on the same or adjacent carbon atoms are taken together to form a $C_{3-8}$-cycloalkyl or $C_{3-7}$-heterocycloalkyl ring and $R_y$ is $C_{1-6}$-alkoxy. In a preferred embodiment, two $R_y$ groups on the same carbon atom are taken together to form a $C_{3-8}$-cycloalkyl or $C_{3-7}$-heterocycloalkyl ring.

Preferred embodiments of Formula II, including pharmaceutically acceptable salts thereof, are shown below in TABLE II below. All compounds of Formula II, as well as pharmaceutically acceptable salts thereof, and the compounds of TABLE II, as well as pharmaceutically acceptable salts thereof, are considered to be "compounds of the invention."

TABLE II

| Compound ID | Structure |
|---|---|
| A-2 | 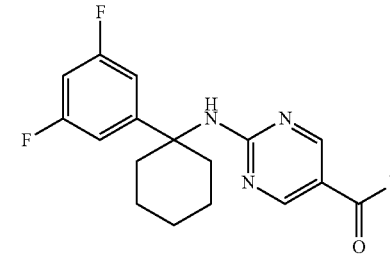 |
| B-2 | 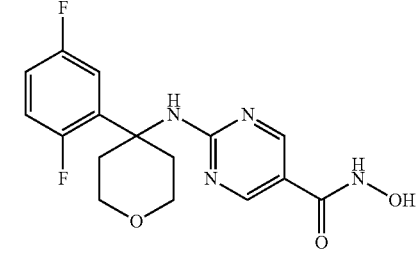 [SMILES: O=C(NO)c1cnc(NC2(c3cc(F)ccc3F)CCOCC2)nc1] |
| C-2 | 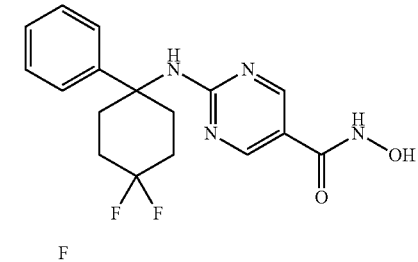 |
| D-2 | 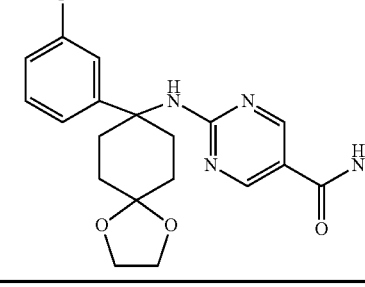 |

The compositions and pharmaceutical compositions provided herein can be used to treat a subject's polycystic disease.

In certain embodiments, the polycystic disease is polycystic liver disease.

In certain embodiments, the polycystic disease is renal cystic disease such as polycystic kidney disease.

In certain embodiments, the compositions and pharmaceutical compositions provided herein can inhibit cholangiocyte proliferation and/or bile duct β-catenin synthesis and/or induce bile duct β-catenin phosphorylation and/or acetylation.

In certain embodiments, the compositions and pharmaceutical compositions provided herein can increase the amount of bile duct acetylated tubulin and/or decrease bile duct β-catenin synthesis.

Another object of the present invention is the use of a compound as described herein in the manufacture of a medicament for use in the treatment of a polycystic disorder or disease herein. Another object of the present invention is the use of a compound as described herein for use in the treatment of a polycystic disorder or disease herein.

Methods of the Invention

In one aspect of the invention, methods for the treatment of polycystic disease are provided, comprising administering a therapeutically effective amount of an HDAC6 specific inhibitor compound of Formula I or II, as described herein, to a subject in need thereof.

A therapeutically effective amount of an HDAC6 specific inhibitor compound of Formula I or II sufficient to treat or ameliorate an effect of a polycystic disease may vary with the nature of the condition being treated, the length of time that activity is desired, and the age and the condition of the patient, and ultimately may be determined by the attendant physician. The amount or dose of an HDAC6 specific inhibitor compound of Formula I or II according to the present invention that may be administered to a patient may also vary depending on a variety of factors known in the art e.g., species, sex, age, weight, condition of the patient, desired response, nature of the condition, metabolism, severity of disease, side-effects. The desired dose may be conveniently administered in a single dose, or as multiple doses administered at appropriate intervals, for example as two, three, four or more sub-doses per day. Multiple doses often are desired, or required.

In certain embodiments, the polycystic disease can be a polycystic liver disease (PLD). PLDs are genetic disorders that can be included in the cholangiopathies, a group of diseases of diverse etiologies all of which have the cholangiocyte as the target cell. PLDs occur either alone or together with polycystic kidney disease (PKD) (see Masyuk et al. Cholangiociliopathies: genetics, molecular mechanisms and potential therapies, Current Opinion in Gastroenterology (2009) 25:265-271).

In certain embodiments, the subject being treated has one or more mutations in at least one of the PRKCSH (Protein Kinase C Substrate 80K-H) and Sec63 genes. These mutations cause polycystic liver disease without kidney involvement (ADPLD) by affecting the cell's posttranslational protein modification machinery and ciliary signal transduction via polycystin-2 degradation ((see Drenth et al. Germline mutations in PRKCSH are associated with autosomal dominant polycystic liver disease, Nature Genetics (2003) 33:345-347 3; Davila et al. Mutations in SEC63 cause autosomal dominant polycystic liver disease, Nat Genet (2004) 36:575-577 4; Woollatt et al. Human Sec63 endoplasmic reticulum membrane protein, map position 6q21, Chromosome Research (1999), 7:77; Gao et al. PRKCSH/ 80K-H, the protein mutated in polycystic liver disease, protects polycystin-2/TRPP2 against HERP-mediated degradation, Human Molecular Genetics (2010) 19:16-24).

In certain embodiments, the subject being treated has one or more mutations in at least on of the Pkd1 and Pkd2 genes, which encode the ciliary-associated proteins, polycystin-1 (PC1) and -2 (PC2), and which are causative for cystic degeneration of the liver and kidneys in autosomal-dominant polycystic kidney disease (ADPKD).

In certain embodiments, the subject being treated has one or more mutations in the Pkhd1 gene which is associated with autosomal-recessive polycystic kidney disease (ARPKD) (see Hughes et al. The polycystic kidney disease 1 (PKD1) gene encodes a novel protein with multiple cell recognition domains, Nature Genetics (1995) 10:151-160; Mochizuki et al. PKD2, a gene for polycystic kidney disease that encodes an integral membrane protein, Science (1996) 272:1339-13428; Onuchic et al. PKHD1, the polycystic kidney and hepatic disease 1 gene, encodes a novel large protein containing multiple immunoglobulin-like plexin-transcription-factor domains and parallel beta-helix 1 repeats, Am J Hum Genet (2002)70:1305-1317; Ward et al. The gene mutated in autosomal recessive polycystic kidney disease encodes a large, receptor-like protein, Nat Genet (2002) 30:259-269).

As used herein, the term "renal cystic disease" includes, but not be limited to, a large group of diseases, including polycystic kidney disease (PCK), von Hippel-Lindau, tuberosclerosis, nephronophthisis, autosomal dominant polycystic kidney disease (ADPKD), autosomal recessive polycystic kidney disease (ARPKD), acquired cystic kidney disease (ACKD), and autosomal dominant polycystic liver disease (ARPKD) (see, for example, Friedman, J. Cystic Diseases of the Kidney, in PRINCIPLES AND PRACTICE OF MEDICAL GENETICS (A. Emery and D. Rimoin, Eds.) pp. 1002-1010, Churchill Livingston, Edinburgh, U. K. (1983); Striker & Striker (1986) Am. J. Nephrol. 6:161-164. Extrarenal manifestations include hepatic and pancreatic cysts as well as cardiovascular complications. Gabow & Grantham (1997) Polycystic Kidney Disease, in DISEASES OF THE KIDNEY (R. Schrier & C. Gottschalk, Eds.), pp. 521-560, Little Brown, Boston; Welling & Grantham (1996) Cystic Diseases of the Kidney, in RENAL PATHOLOGY (C. Tisch & B. Brenner, Eds.) pp:1828-1863, Lippincott, Philadelphia).

In another aspect, a therapeutically effective amount of a compound of Formula I or II is injected intraperitoneally into a subject with a polycystic disease, wherein the compound of Formula I or II treats the polycystic disease.

In certain embodiments, the HDAC6-specific inhibitor compound of Formula I or II prevents cyst formation.

In certain embodiments, the HDAC6-specific inhibitor compound of Formula I or II inhibits cyst growth.

In certain embodiments, the HDAC6-specific inhibitor compound of Formula I or II inhibits cholangiocyte proliferation.

HDAC6 inhibition with a compound of Formula I or II can decrease many hallmarks of polycystic liver disease including hepatomegaly and the growth of cysts in the liver or kidney.

In certain embodiments, HDAC6 inhibition with a compound of Formula I or II prevents the formation of cysts in patients that are genetically pre-disposed to acquiring a polycystic disease.

In a preferred embodiment, the compound of Formula I can be Compound A-1.

In a preferred embodiment, the compound of Formula I can be Compound B-1.

In a preferred embodiment, the compound of Formula II can be Compound C-2.

In certain embodiments, pharmacological inhibition of HDAC6 with a compound of Formula I or II treats polycystic disease by inhibiting β-catenin function e.g. inhibiting the expression of and nuclear accumulation of β-catenin.

In one aspect of the invention, a method for the treatment of polycystic liver disease is provided comprising administering to a subject with polycystic liver disease a therapeutically effective amount of the HDAC6 specific inhibitor compound (Compound A-1) having the structure of:

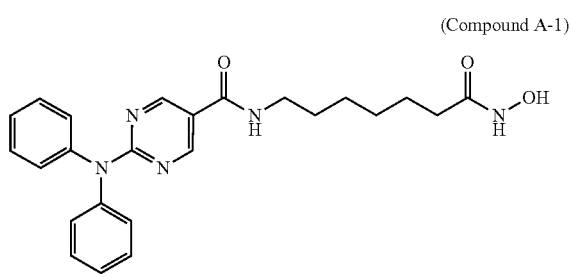 [SMILES: O=C(CCCCCCNC(=O)c1cnc(N(c2ccccc2)c2ccccc2)nc1)NO]

(Compound A-1)

or pharmaceutically acceptable salts thereof, wherein the amount of the HDAC6 specific inhibitor compound A-1 is effective at inhibiting cyst growth.

In one aspect of the invention, a method for the treatment of polycystic liver disease is provided comprising administering to a subject with polycystic liver disease a therapeutically effective amount of the HDAC6 specific inhibitor compound B-1 having the structure of:

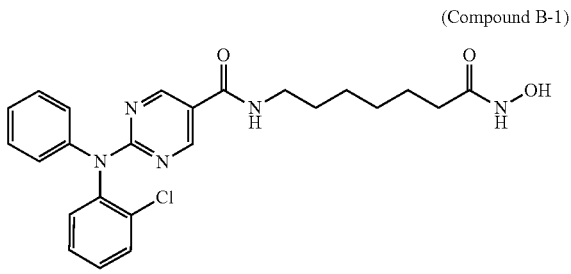 [SMILES: O=C(CCCCCCNC(=O)c1cnc(N(c2ccccc2)c2ccccc2Cl)nc1)NO]

(Compound B-1)

or pharmaceutically acceptable salts thereof, wherein the amount of the HDAC6 specific inhibitor compound B-1 is effective at inhibiting cyst growth.

In one aspect of the invention, a method for the treatment of polycystic liver disease is provided comprising administering to a subject with polycystic liver disease a therapeutically effective amount of the HDAC6 specific inhibitor compound C-2 having the structure of:

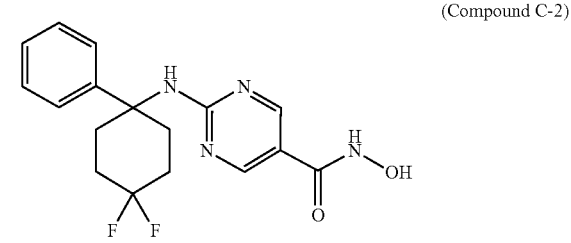 [SMILES: O=C(NO)c1cnc(NC2(c3ccccc3)CCC(F)(F)CC2)nc1]

(Compound C-2)

or pharmaceutically acceptable salts thereof, wherein the amount of the HDAC6 specific inhibitor compound C-2 is effective at inhibiting cyst growth.

Pharmaceutical Compositions

In another aspect, the invention provides a pharmaceutical composition comprising a compound of Formula I or II, or a pharmaceutically acceptable ester, salt, or pro-drug thereof, together with a pharmaceutically acceptable carrier. This pharmaceutical composition can be used in the treatment of polycystic diseases.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent, anticancer agent or agent useful for the treatment of an autoimmune disease such as SLE), or they may achieve different effects (e.g., control of any adverse effects).

In certain embodiments, the pharmaceutical compositions of the present invention further comprise one or more additional therapeutically active ingredients. For purposes of the invention, the term "palliative" refers to treatment that is focused on the relief of symptoms of a disease and/or side effects of a therapeutic regimen, but is not curative. For example, palliative treatment encompasses painkillers, anti-nausea medications, anti-pyretics, and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

The pharmaceutical compositions of the present invention comprise a therapeutically effective amount of a compound of the present invention formulated together with one or more pharmaceutically acceptable carriers.

As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

According to the methods of treatment of the present invention, disorders are treated or prevented in a subject, such as a human or other animal, by administering to the subject a therapeutically effective amount of a compound of the invention, in such amounts and for such time as is necessary to achieve the desired result.

The term "therapeutically effective amount" of a compound of the invention, as used herein, means a sufficient amount of the compound so as to decrease one or more of the symptoms caused by a polycystic liver disease in a subject.

As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight (0.05 to 4.5 mg/m$^2$). An indicated daily dosage in the larger mammal, e.g. humans, is in the range from about 0.5 mg to about 100 mg, conveniently administered, e.g. in divided doses up to four times a day or in controlled release form. Suitable unit dosage forms for oral administration comprise from ca. 1 to 50 mg active ingredient.

In certain embodiments, a therapeutic amount or dose of the compounds of the present invention may range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of symptoms resulting from the polycystic liver disease.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Kits

The disclosure herein provides for a kit format which comprises package units having different doses of the compound of Formula I or II for treating a polycystic disease in a subject. In certain embodiments, the compound of Formula I is the compound A-1 or compound B-1. In other embodiments, the compound of Formula II is the compound C-2.

The kit may also contain one or more of the following items: instructions for use including prescribing information, dosage information, storage information, and the like as well as sterile saline solution, needles, syringes, catheters and first aid materials such as bandages etc. Kits may include containers of reagents mixed together in suitable proportions for performing the methods described herein.

Reagent containers preferably contain reagents in unit quantities that obviate measuring steps when performing the subject methods.

The package label can include, for example, instructions to take the compound of Formula I or II for the treatment of a polycystic disease. In another embodiment, the package label includes instructions to treat polycystic liver disease.

Packaged compositions are also provided that comprise a therapeutically effective amount of a compound of Formula I or Formula II, and a pharmaceutically acceptable carrier or diluent as well as instructions on how to treat a polycystic disease such as polycystic liver disease.

Compounds of the present invention can be conveniently prepared or formed during the process of the invention, as solvates (e.g., hydrates). Hydrates of compounds of the present invention can be conveniently prepared by recrystallization from an aqueous/organic solvent mixture, using organic solvents such as dioxan, tetrahydrofuran or methanol.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). The compounds of this invention may also be represented in multiple tautomeric forms, in such instances, the invention expressly includes all tautomeric forms of the compounds described herein. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment herein includes that embodiment as any single embodiment or in combination with any other embodiments or portions thereof. The recitation of an embodiment for a variable herein includes that embodiment as any single embodiment or in combination with any other embodiments or portions thereof.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the chemical structures, substitutents, derivatives, formulations and/or methods of the invention may be made without departing from the spirit of the invention and the scope of the appended claims. Definitions of the variables in the structures in the schemes herein are commensurate with those of corresponding positions in the formulae presented herein.

Example 1: Synthesis of the Compounds of the Invention

The synthesis of the compounds of Formula I is provided in PCT/US2011/021982, which is incorporated herein by reference in its entirety.

Synthesis of Compound A-1

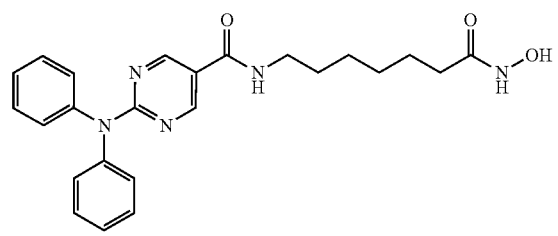 [SMILES: O=C(CCCCCCNC(=O)c1cnc(N(c2ccccc2)c2ccccc2)nc1)NO]

Reaction Scheme

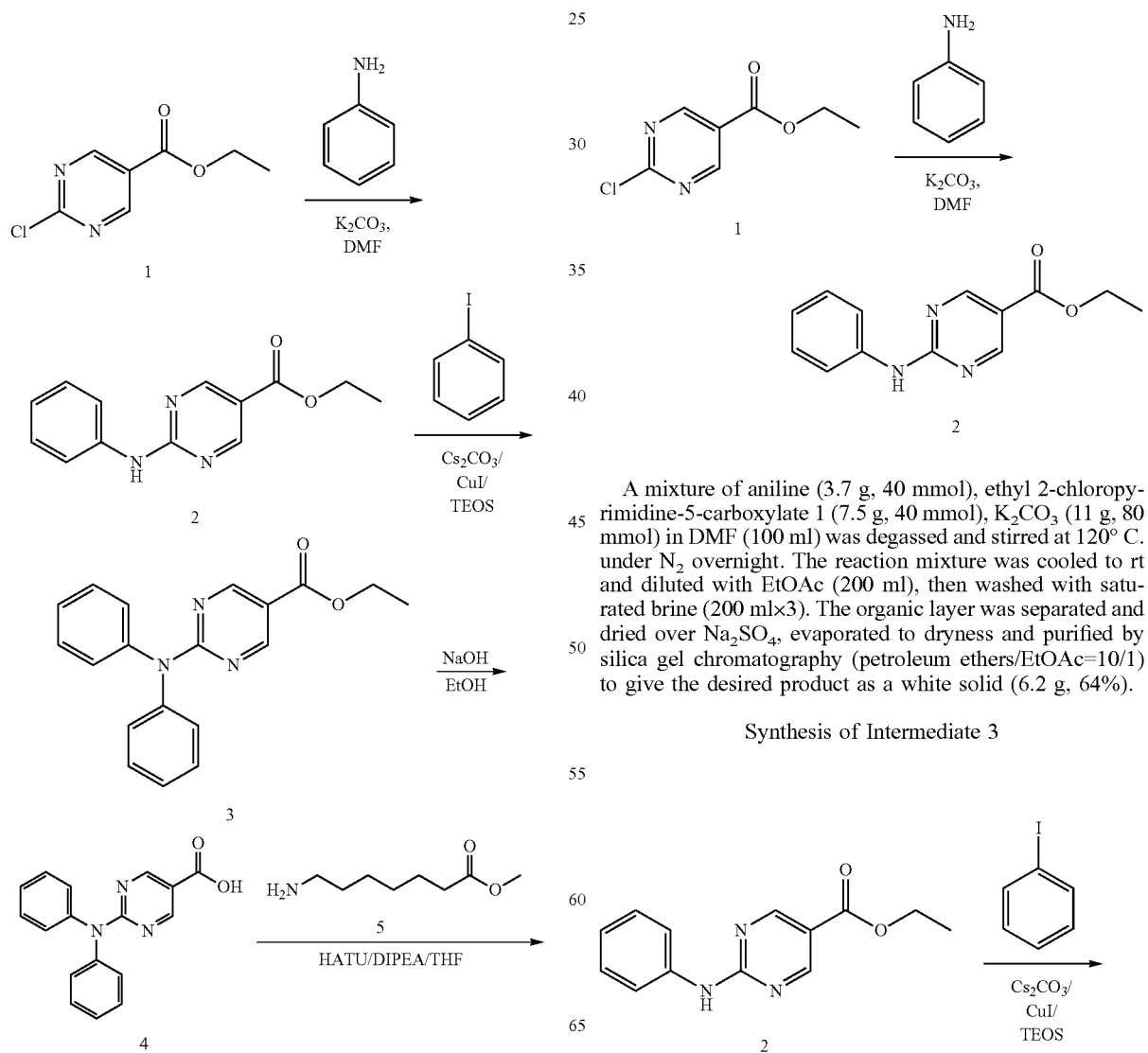

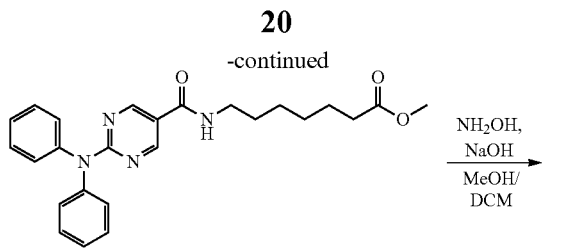

Synthesis of Intermediate 2

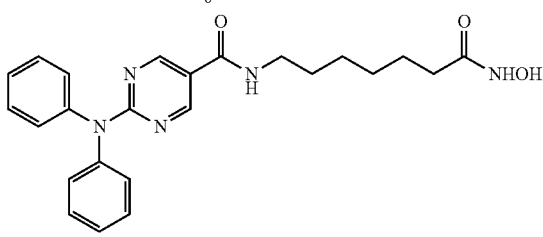

A mixture of aniline (3.7 g, 40 mmol), ethyl 2-chloropyrimidine-5-carboxylate 1 (7.5 g, 40 mmol), $K_2CO_3$ (11 g, 80 mmol) in DMF (100 ml) was degassed and stirred at 120° C. under $N_2$ overnight. The reaction mixture was cooled to rt and diluted with EtOAc (200 ml), then washed with saturated brine (200 ml×3). The organic layer was separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3

22

Synthesis of Intermediate 6

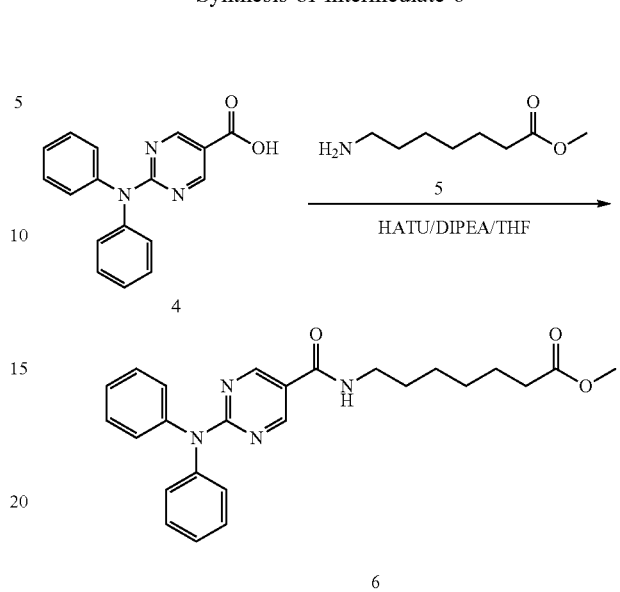

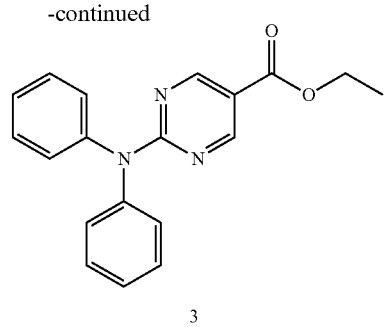

A mixture of the compound 2 (6.2 g, 25 mmol), iodobenzene (6.12 g, 30 mmol), CuI (955 mg, 5.0 mmol), Cs₂CO₃ (16.3 g, 50 mmol) in TEOS (200 ml) was degassed and purged with nitrogen. The resulting mixture was stirred at 140° C. for 14 h. After cooling to r.t., the residue was diluted with EtOAc (200 ml) and 95% EtOH (200 ml), NH₄F—H₂O on silica gel [50 g, pre-prepared by the addition of NH₄F (100 g) in water (1500 ml) to silica gel (500 g, 100-200 mesh)] was added, and the resulting mixture was kept at r.t. for 2 h, the solidified materials was filtered and washed with EtOAc. The filtrate was evaporated to dryness and the residue was purified by silica gel chromatography (petroleum ethers/EtOAc=10/1) to give a yellow solid (3 g, 38%).

A mixture of compound 4 (2.5 g, 8.58 mmol), aminoheptanoate 5 (2.52 g, 12.87 mmol), HATU (3.91 g, 10.30 mmol), DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of Intermediate 4

Synthesis of 2-(diphenylamino)-N-(7-(hydroxyamino)-7-oxoheptyl)pyrimidine-5-carboxamide

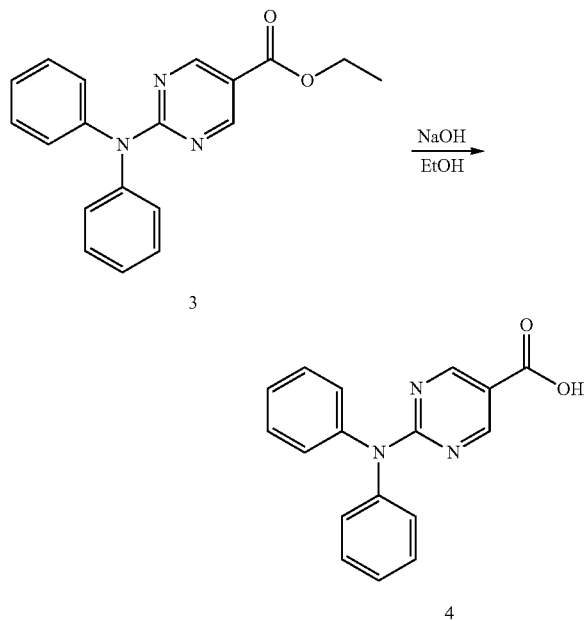

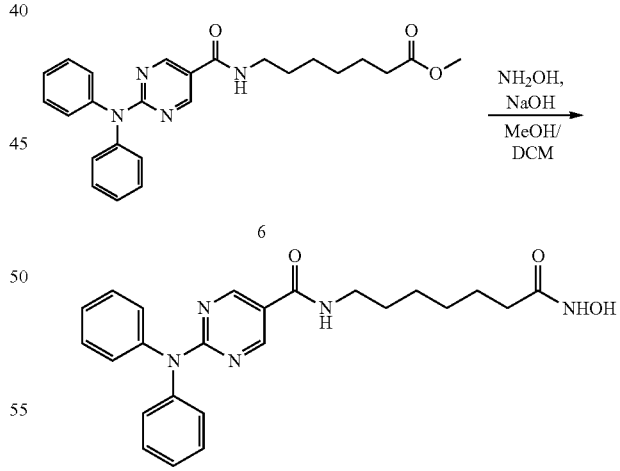

2N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over Na₂SO₄. Removal of solvent gave a brown solid (2.5 g, 92%).

A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

Synthesis of Compound B-1

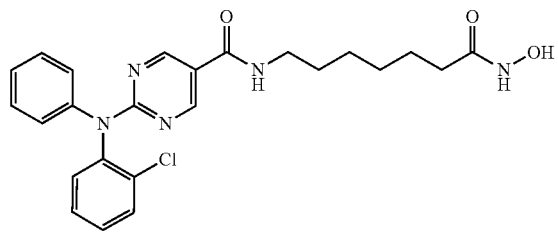 [SMILES: O=C(CCCCCCNC(=O)c1cnc(N(c2ccccc2)c2ccccc2Cl)nc1)NO]

Reaction Scheme:

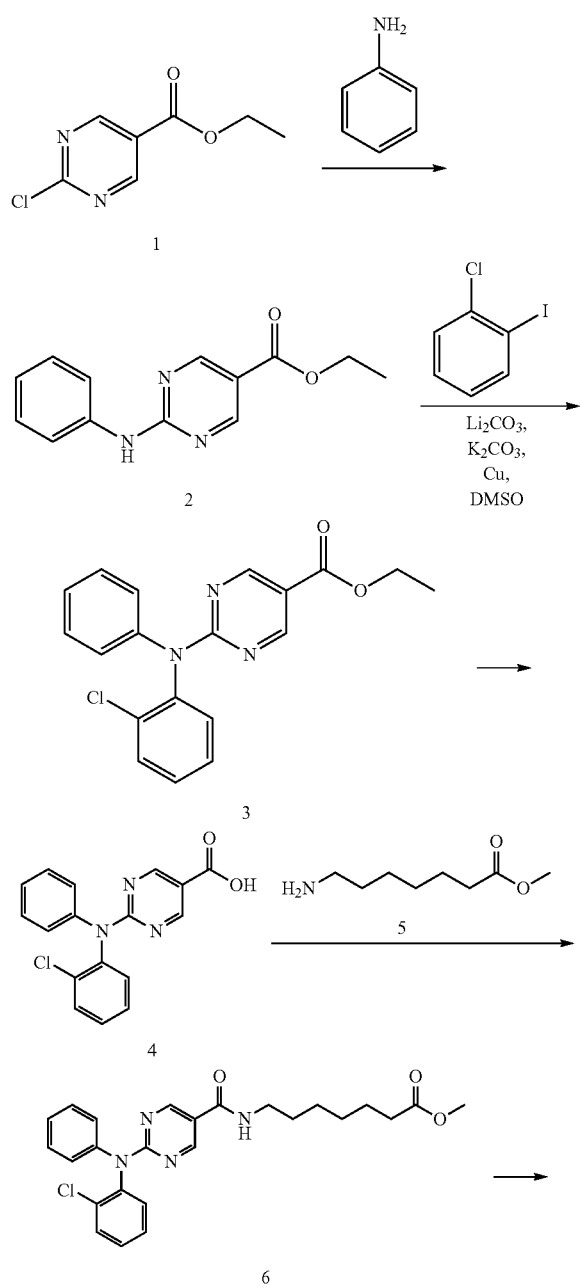

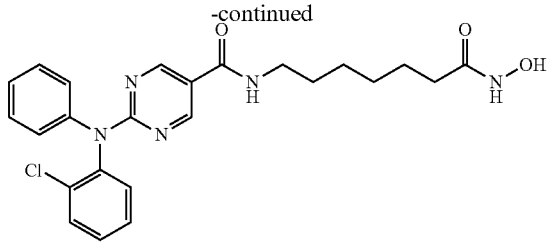

Synthesis of Intermediate 2: See synthesis of intermediate 2 in synthesis of Compound A-1 above.

Synthesis of Intermediate 3

A mixture of compound 2 (69.2 g, 1 equiv.), 1-chloro-2-iodobenzene (135.7 g, 2 equiv.), $Li_2CO_3$ (42.04 g, 2 equiv.), $K_2CO_3$ (39.32 g, 1 equiv.), Cu (1 equiv. 45 μm) in DMSO (690 ml) was degassed and purged with nitrogen. The resulting mixture was stirred at 140° C. Work-up of the reaction gave compound 3 at 93% yield.

Synthesis of Intermediate 4: See synthesis of intermediate 4 in synthesis of Compound A-1 above.

Synthesis of Intermediate 6: See synthesis of intermediate 6 in synthesis of Compound A-1 above.

Synthesis of 2-((2-chlorophenyl)(phenyl)amino)-N-(7-(hydroxyamino)-7-oxoheptyl)pyrimidine-5-carboxamide (Compound B-1)

See synthesis of Compound A-1 above.

Another embodiment is a method of making a compound of Formula I using any one, or combination of, reactions delineated herein. The method can include the use of one or more intermediates or chemical reagents delineated herein.

Synthesis of Compound C-2

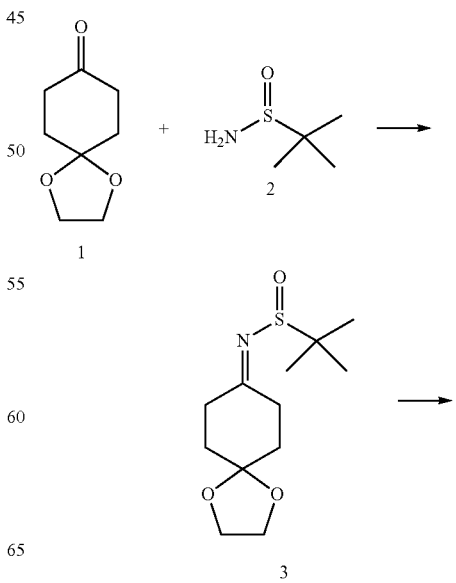

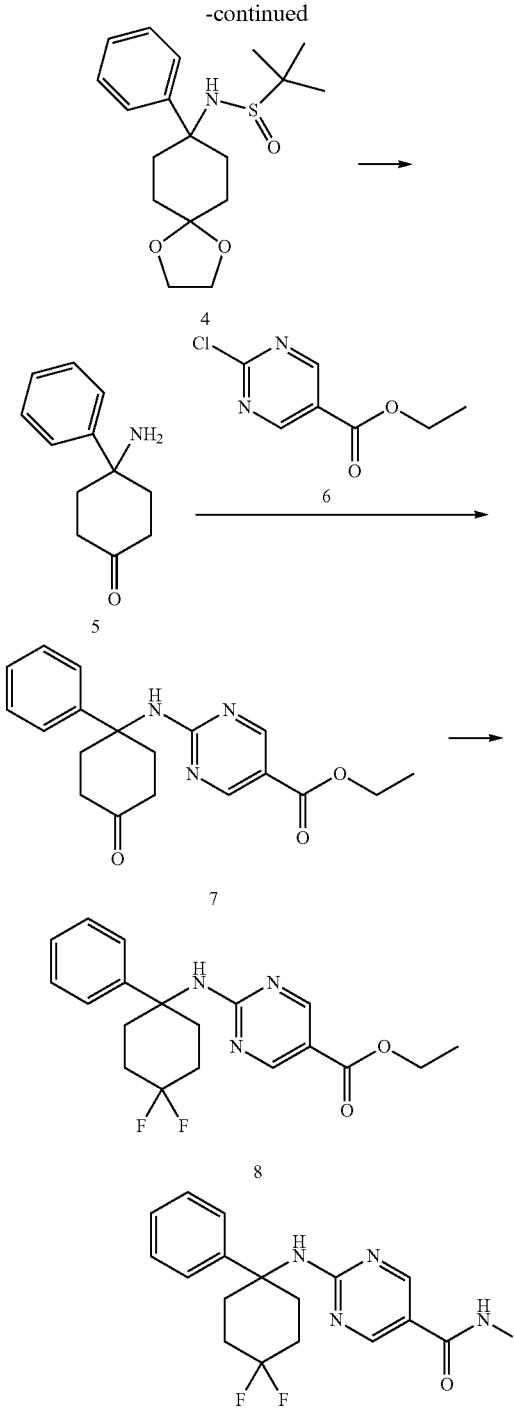

Step 1: To a solution of 1 (2.00 g, 12.81 mmol) and 2 (1.552 g, 12.81 mmol) in THF (20 mL) was added Ti(OEt)$_4$ (5.4 mL, 25.56 mmol). The mixture was stirred at r.t. for 16 hrs and then poured into saturated NaHCO$_3$ solution at 0° C. The resulting precipitate was filtered off. The resulting filtrate was extracted with EA. The combined EA layers were concentrated in vacuo and the residue was purified by silica gel chromatography (PE/EA=4/1, 2/1) to afford 3 as a white solid (2.61 g, yield: 75%).

Step 2: To a flask containing 3 (1.00 g, 3.86 mmol) was added a solution of PhMgBr (1M in THF, 10 mL) at 0° C. It was stirred at 0° C. to rt until a complete reaction. Saturated NH$_4$Cl solution was added to adjust pH 6-7. The resulting mixture was extracted with EA. The combined EA layers were concentrated in vacuo and the residue was purified by silica gel chromatography (PE/EA=5/1, 2/1, 1.5/1) to afford 4 as a white solid (823 mg, yield: 60%).

Step 3: A mixture of compound 4 (8.3 mg, 2.38 mmol) in HCl (2M in water, 20 mL) and THF (20 mL) was stirred at 50° C. for 16 hrs. A solution of NaOH was added to the mixture to adjust pH 7-8. THF was removed in vacuo and the aqueous phase was extracted with EA. The combined EA layers were concentrated in vacuo and the residue was dissolved in EA. HCl (4 M, 1 mL) was added. The resulting white solid was collected by filtration to afford desired product 5 (395 mg, yield: 57%).

Step 4: A mixture of compound 5 (350 mg, 1.55 mmol), 6 (376 mg, 2.02 mol), and DIPEA (1.07 mL, 6.47 mmol) in NMP (4 mL) was stirred at 130° C. for 5 hrs. The mixture was added water (20 mL), extracted with EA (25 mL×2). The organic layer was concentrated to get a residue, which was purified by silica gel chromatography (PE/EA=4/1) to afford 7 (178 mg, yield: 34%).

Step 5: To a solution of compound 7 (168 mg, 0.50 mmol) in DCM (30 mL) was added DAST (302 μL, 2.47 mmol) at 0° C. It was stirred at rt for 3 hrs and 35° C. for 2 hrs. The reaction mixture was quenched with saturated NaHCO$_3$ (5 mL), and extracted with EtOAc (2×5 mL). The organic extracts were concentrated in vacuo. The residue was purified by pre-TLC to give 8 (74 mg, yield: 42%).

Step 6: NH$_2$OH (50% in water, 3.9 mL) was added to a flask containing 8 (74 mg, 0.20 mmol) at 0° C. Then saturated NaOH solution in MeOH (3.9 ml) was added at 0° C. DCM (3.9 mL) was added to aid substrate to dissolve. The mixture was heated at 25° C. for 18 hrs. Con. HCl was added to adjust pH to 7. It was concentrated in vacuo and the residue was purified by pre-HPLC to afford Compound C-2 (27 mg, yield: 38%) as a white solid. $^1$H NMR (500 MHz, DMSO) δ 10.96 (s, 1H), 9.00 (s, 1H), 8.63 (s, 1H), 8.35 (s, 1H), 8.29 (s, 1H), 7.39 (d, J=7.6 Hz, 2H), 7.28 (t, J=7.7 Hz, 2H), 7.17 (t, J=7.3 Hz, 1H), 2.73 (s, 2H), 2.23-1.88 (m, 6H). LCMS: m/z=349 (M+H)$^+$.

Example 2: HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 μM TCEP) to 6 fold their final concentration. The HDAC enzymes (purchased from BPS Biosciences) were diluted to 1.5 fold their final concentration in assay buffer. The tripeptide substrate and trypsin at 0.05 μM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 μM (HDAC1), 10 μM (HDAC2), 17 μM (HDAC3) and 14 μM (HDAC6).

Five μl of compounds and 20 μl of enzyme were added to wells of a black, opaque 384 well plate in duplicate. Enzyme and compound were incubated together at room temperature for 10 minutes. Five μl of substrate was added to each well, the plate was shaken for 60 seconds and placed into a Victor 2 microtiter plate reader. The development of fluorescence was monitored for 60 min and the linear rate of the reaction was calculated. The IC50 was determined using Graph Pad Prism by a four parameter curve fit. The IC50 values (nM) obtained for the compound C-2 can be found in TABLE III, below.

TABLE III

| Compound ID | Structure | HDAC1 | HDAC2 | HDAC3 | HDAC6 |
|---|---|---|---|---|---|
| C-2 | 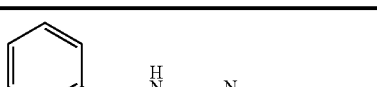 | 961 | 982 | 4380 | 3.7 |

The IC50 values (nM) obtained for compounds A-1 and B-1 can be found in TABLE I.

Example 3: HDAC6 is Overexpressed in Cystic Cholangiocytes

Polymerase Chain Reaction

RNA was isolated from control and PCK rat cholangiocytes with TRIZOL reagent (Invitrogen). cDNA was obtained using First Srand cDNA Synthesis (Invitrogen) reagents and HDAC6 primers (forward primer: 5'-TCA GCG CAG TCT TAT GGA TG-3' (SEQ ID NO.: 1); reverse primer: 5'-GCG GTG GAT GGA GAA ATA GA-3', SEQ ID NO.: 2) were purchased from Integrated DNA Technologies. β-catenin mRNA expression was analyzed using the TaqMan Gene Expression Assay (Assay ID Rn00584431_g1) following the manufacturer directions. The samples were normalized to 18S rRNA.

Western Blots

Protein isolated from cultured control rat and PCK rat cholangiocytes were analyzed. Cells were scrapped, resuspended in Phosphate Buffered Saline (PBS) with Protease Inhibitors, Sodium Orthovanadate and Phenylmethanesulfonylfluoride (PMSF), sonicated and equal amounts of sample protein were diluted in Laemmli Sample Buffer (Biorad) and mercaptoethanol. After SDS polyacrylamide gel electrophoresis, SDS-PAGE, proteins were transferred to nitrocellulose membranes, blocked, and then incubated with the following primary antibodies: HDAC6 (Santa Cruz Biotechnology, D-11, 1:500), acetylated-α-tubulin (Sigma Aldrich, 1:2000), β-catenin (Cell Signaling Technology, (D10A8) XP® Rabbit mAb; 1:1000), Phospho-β-Catenin (Ser33/37/Thr41) (Cell Signaling Technology, 1:1000), acetyl-β-catenin (Cell Signaling Technology, 1:1000), c-myc (Santa Cruz Biotechnology, 1:500), cyclin D1 (Santa Cruz Biotechnology, 1:500), and actin (Sigma Aldrich, 1:5000). The membranes were incubated overnight at 4° C., washed and incubated for 1 hour at room temperature with horseradish perodixase-conjugated (1:5000, Invitrogen) or IRdye 680 or 800 (1:15000, Odyssey) corresponding secondary antibody. The ECL system or Odyssey Licor Scanner was used for protein detection and the Gel-Pro Analyzer 6.0 software was used for densitometry analysis.

Immunofluorescence and Confocal Microscopy.

Paraffin-embedded liver sections of control and PCK rats, healthy human beings, and ADPKD and ARPKD patients were incubated with antibodies against HDAC6 (Santa Cruz Biotechnology, D-11, 1:100) and acetylated-α-tubulin (Sigma Aldrich, mouse monoclonal 1:500) overnight at 4° C. followed by 90 minutes at room temperature of fluorescent secondary antibody incubation. Nuclei were stained with DAPI (ProLong Gold Antifade Reagent, Life Technologies). Images were acquired with a Zeiss LSM 510 confocal microscope. Paraffin blocks from 3 normal, 3 ARPKD, and 3 ADPKD patients were obtained from the Mayo Clinic Tissue Registry Archives. All experimental procedures were approved by the Mayo Clinic Institutional Review Boards (IRB #: 08-005681).

Statistics

Data are expressed as mean±SE. Statistical analyses were conducted by two-tailed; Student's t-tests were used to compare two groups. The cut-off p-value for significance was set at p<0.05.

To assess the expression of HDAC6 mRNA in cholangiocytes, mRNA isolated from cultured rat cholangiocytes was analyzed using PCR. As shown in FIG. 1A, HDAC6 mRNA is present in both control and PCK rat cholangiocytes. The identity of the PCR product was confirmed by sequencing.

Figure 1B:
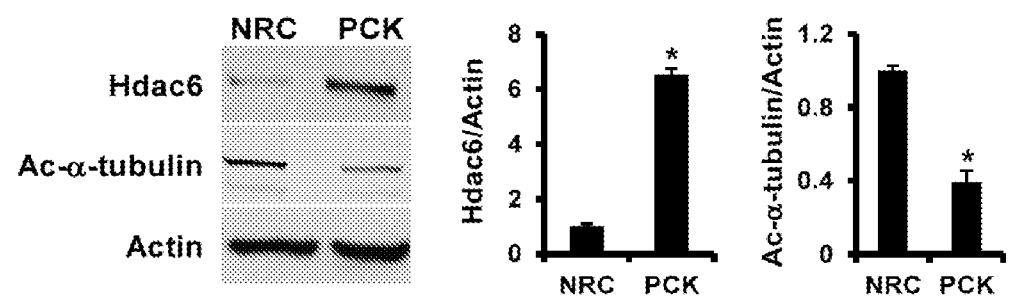

FIG. 1B shows a Western blot analysis on proteins isolated from cultured control rat and PCK rat cholangiocytes. HDAC6 protein is overexpressed 6.5-fold in PCK cholangiocytes compared to control rat cholangiocytes, which correlates with decreased levels of acetylated-α-tubulin, one of the principal HDAC6 substrates (see Zhang et al. Two catalytic domains are required for protein deacetylation, J. Biol. Chem. (2006) 281:2401-2404).

Figure 1C:
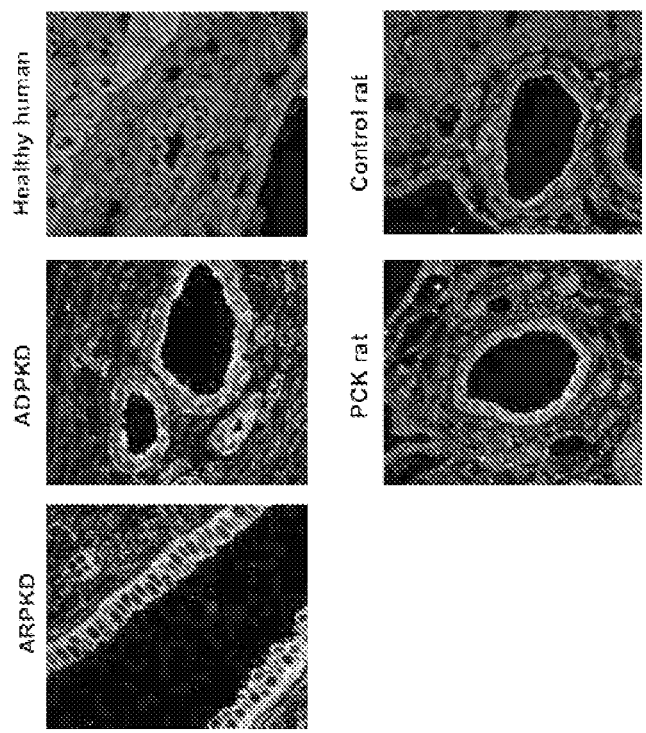

The overexpression of HDAC6 observed in vitro was also confirmed in vivo by confocal immunofluorescence of liver tissues. In liver tissues of PCK rats, as well as ADPKD and ARPKD patients, the immunoreactivity of HDAC6 is increased in hepatic cysts compared to normal rats and healthy human controls, respectively (FIG. 1C).

Example 4: Inhibition of HDAC6 Decreases Cholangiocyte Proliferation and Cysts Growth In Vitro Tissue Culture For in vitro experiments, cholangiocytes were isolated from control rats, PCK rats (an animal model for ARPKD; Vroman B, LaRusso N F: Development and characterization of polarized primary cultures of rat intrahepatic bile duct epithelial cells, Lab Invest 1996, 74:303-313), healthy human beings and ADPKD patients (Masyuk et al. Biliary exosomes influence cholangiocyte regulatory mechanisms and proliferation through interaction with primary cilia, Am J Physiol Gastrointest Liver Physiol (2010) 299:G990-999; O'Hara et al. Cholangiocyte N-Ras protein mediates lipopolysaccharide-induced interleukin 6 secretion and proliferation, J Biol Chem (2011) 286:30352-30360; Banales et al.

Up-regulation of microRNA 506 leads to decreased Cl(−)/HCO(3) (−) anion exchanger 2 expression in biliary epithelium of patients with primary biliary cirrhosis, Hepatology (2012) 56(2):687-97).

Cholangiocytes were cultured in Collagen-I-coated flasks (BD Biocoat). All cell lines were incubated in NRC Media at 37° C., 5% CO2, 100% humidity. NRC Media contains Dulbecco's modified Eagle medium/F12 with the following additions: 0.01 mL/mL Minimum Essential Media (MEM) nonessential amino acids, 0.01 mL/mL lipid concentrate, 0.01 mL/mL MEM vitamin solution, 2 mmol/L L-glutamine, 0.05 mg/mL soybean trypsin inhibitor, 0.01 mL/mL insulin/transferring/selenium-S, 5% fetal bovine serum, 30 g/mL bovine pituitary extract, 25 ng/mL epidermal growth factor, 393 ng/mL dexamethasone, 3.4 g/mL 3,3-,5-triiodo-L-thyronine, 4.11 g/mL forskolin, and 1% penicillin-streptomycin.

Proliferation Assays

Control and PCK rat cholangiocytes were cultured on Collagen-I-coated flasks (BD Biocoat) using NRC Media, detached with 0.25% Trypsin-EDTA (GIBCO), transferred to Collagen-I-coated 96-well plates (10 000 cells/well) and incubated at 37° C., 5% $CO_2$, 100% humidity. Treatment with 5, 10 and 20 μmon Tubastatin A (Chemie Tek), 1-2 μmon Tubacin (Chemie Tek), or 2, 4, and 8 μmon Compound A-1 (Acetylon Pharmaceutical Inc.) suspended in NRC media was started 24 hours later. The drug vehicle, DMSO, was suspended in NRC Media as a control. Cell proliferation was assessed with the CellTiter 96 AQueous One Solution (MTS; Promega) and/or counting cells using the Cellometer Auto T4 Cell Counter (Nexcelom Bioscience).

3D-Culture

Freshly isolated bile ducts from PCK rats were embedded in a rat-tail type I Collagen matrix (BD Biosciences) and grown in the presence or absence of 10 μmon Tubastatin A and 2 μmon Tubacin. Images of the growing cysts were taken every day over a period of 5 days and cyst size was measured with the software "Image J" (National Institute of Health). The circumferential areas for each cystic structure was compared to day 0 to calculate percentages of growth as previously described (see Muff et al. Development and characterization of a cholangiocyte cell line from the PCK rat, an animal model of Autosomal Recessive Polycystic Kidney Disease, Lab Invest 2006, 86:940-950; Masyuk et al. Octreotide inhibits hepatic cystogenesis in a rodent model of polycystic liver disease by reducing cholangiocyte adenosine 3',5'-cyclic monophosphate, Gastroenterology (2007) 132:1104-1116 27; Lee et al. MicroRNA15a modulates expression of the cell-cycle regulator Cdc25A and affects hepatic cystogenesis in a rat model of polycystic kidney disease, J. Clin. Invest. (2008) 118:3714-3724 28. Gradilone et al. Activation of Trpv4 reduces the hyperproliferative phenotype of cystic cholangiocytes from an animal model of ARPKD, Gastroenterology (2010) 139:304-314 e302).

PCK cholangiocytes proliferate at a higher rate than control rat cholangiocytes (see Banales J M, Masyuk T V, Gradilone S A, Masyuk A I, Medina J F, LaRusso N F: The cAMP effectors Epac and protein kinase a (PKA) are involved in the hepatic cystogenesis of an animal model of autosomal recessive polycystic kidney disease (ARPKD), Hepatology 2009, 49:160-174). To test if up regulation of HDAC6 contributes to cholangiocyte hyperproliferation, the HDAC6 selective inhibitor tubastatin-A was added to cultured cholangiocytes.

Figure 2A:
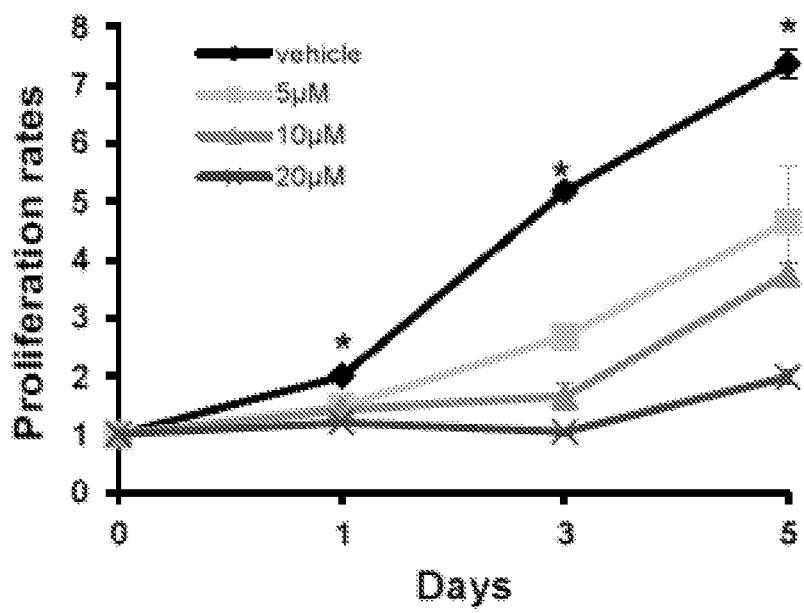
FIGS. 2A-2D shows HDAC6 inhibition decreases cystic cholangiocytes proliferation and cystic growth. Cells were incubated in 96-well plates and proliferation was analyzed by MTS assay.
Figure 2B:
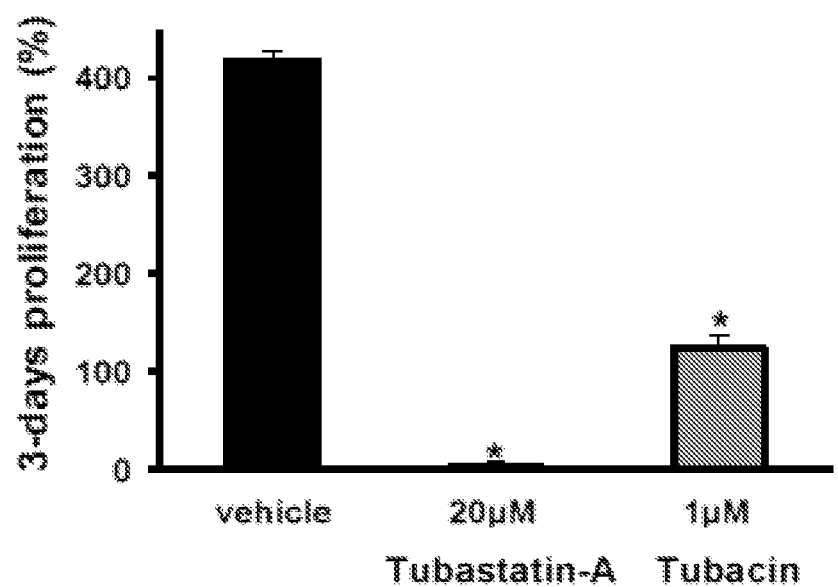
Figure 5A:
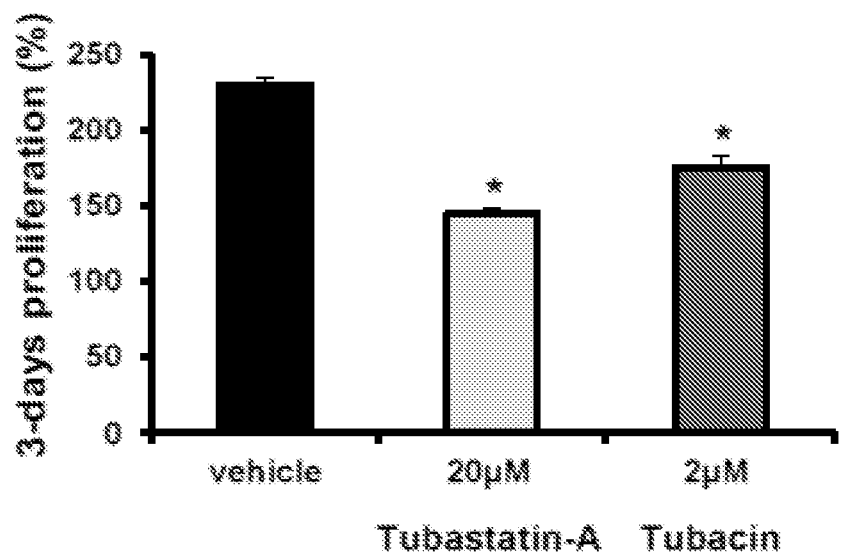
FIG. 5A depicts a human ADPKD 3-day proliferation assay showing decreased proliferation induced by both HDAC6 specific inhibitors, tubastatin-A and tubacin.
Figure 5B:
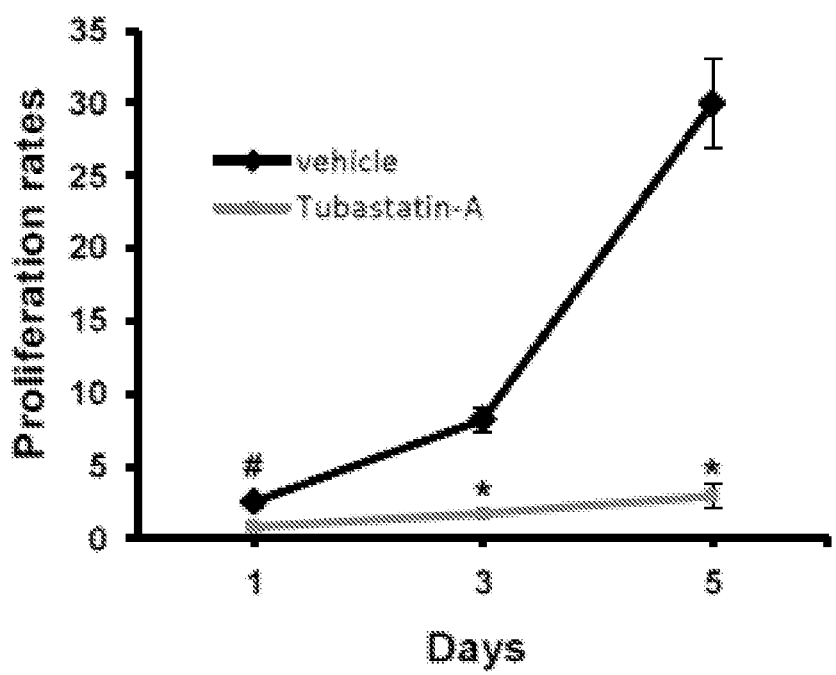
FIG. 5B depicts a PCK cells proliferation analysis by cell counting showing the effect of 20 μM tubastatin A.

FIG. 2A shows that tubastatin-A decreased PCK cholangiocyte proliferation in a dose and time dependent fashion. By day 3, proliferation of treated PCK cholangiocytes was reduced by 2.5-, 3.5-, and 4.15-folds for 5 μM, 10 μM and 20 μM tubastatin A, respectively. Additionally, a different HDAC6 specific inhibitor, tubacin, also reduced PCK cholangiocyte proliferation by 2.94-folds (FIG. 2B). Both drugs also decreased proliferation of cultured human ADPKD cholangiocytes by 85% and 16%, respectively (FIG. 5A). To further confirm the effect of HDAC6 inhibition on proliferation, HDAC6 inhibitor tubastatin-A significantly reduces cystic cholangiocyte proliferation as measured using a Cellometer Auto T4 Cell (FIG. 5B).

Figure 2C:
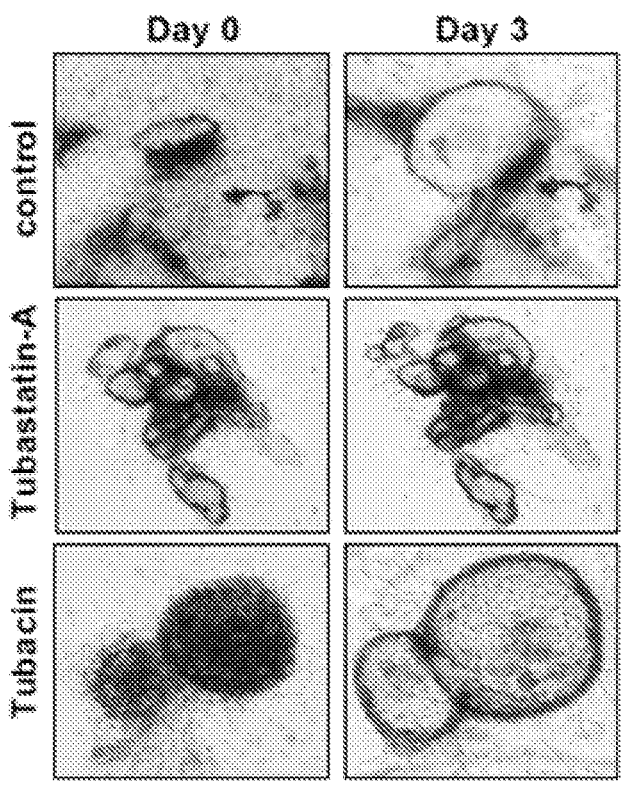
Figure 2D:
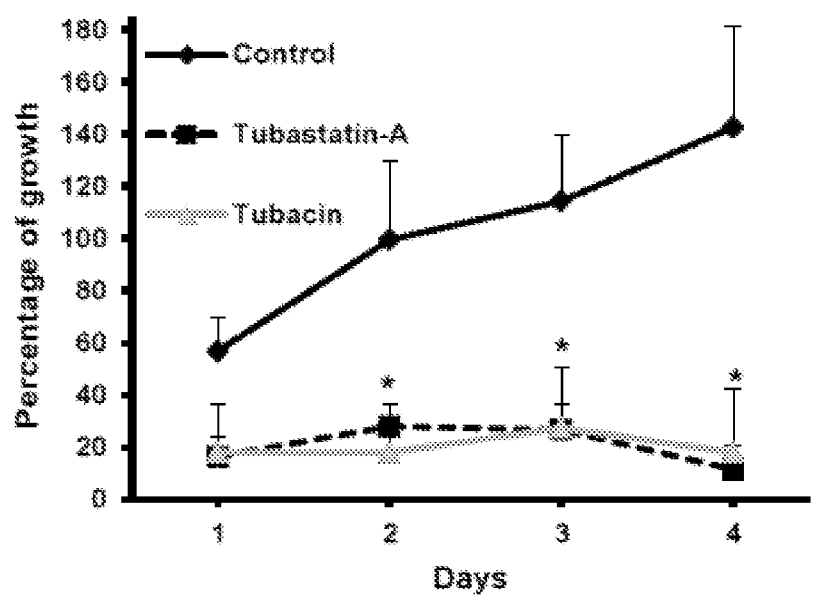

Liver cysts isolated from the PCK rat and grown in a 3-D collagen matrix were treated with HDAC6 inhibitors (FIG. 2C). Analysis of the circumferential areas of the PCK cystic structures showed significant inhibition of cyst growth. After four days of drug administration, tubastatin-A and tubacin reduced cyst growth by 131% and 125%, respectively compared to untreated cysts (FIG. 2D).

Example 5: Inhibition of HDAC6 Decreases β-Catenin Protein Levels

For a better understanding of the mechanisms that are responsible for the inhibition of PCK cholangiocyte proliferation and cyst growth in 3D culture, cultured PCK cholangiocytes were treated with tubastatin-A and tubacin and the amount of acetylated α-tubulin and β-catenin was determined by Western blotting.

Figure 3A:
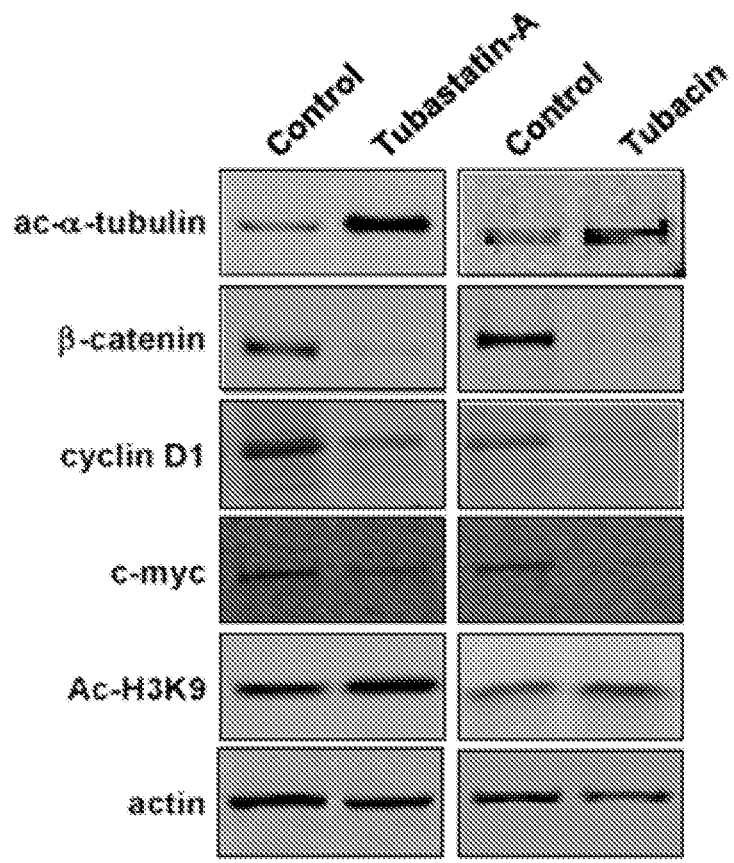
FIGS. 3A-3C shows HDAC6 inhibitors increase acetylated α-tubulin and decrease β-catenin. PCK cholangiocytes were treated with 20 μM Tubastatin A or 2 μM Tubacin, lysed and used for Western blotting.

PCK cholangiocytes treated with tubastatin-A and tubacin had increased levels of acetylated α-tubulin (13- and 2.3-fold) compared to untreated cells (FIG. 3A). In contrast, the levels of β-catenin were decreased by 2.2-, and 5-fold after treatment with tubastatinA and tubacin, respectively (FIG. 3A).

Figure 6A:
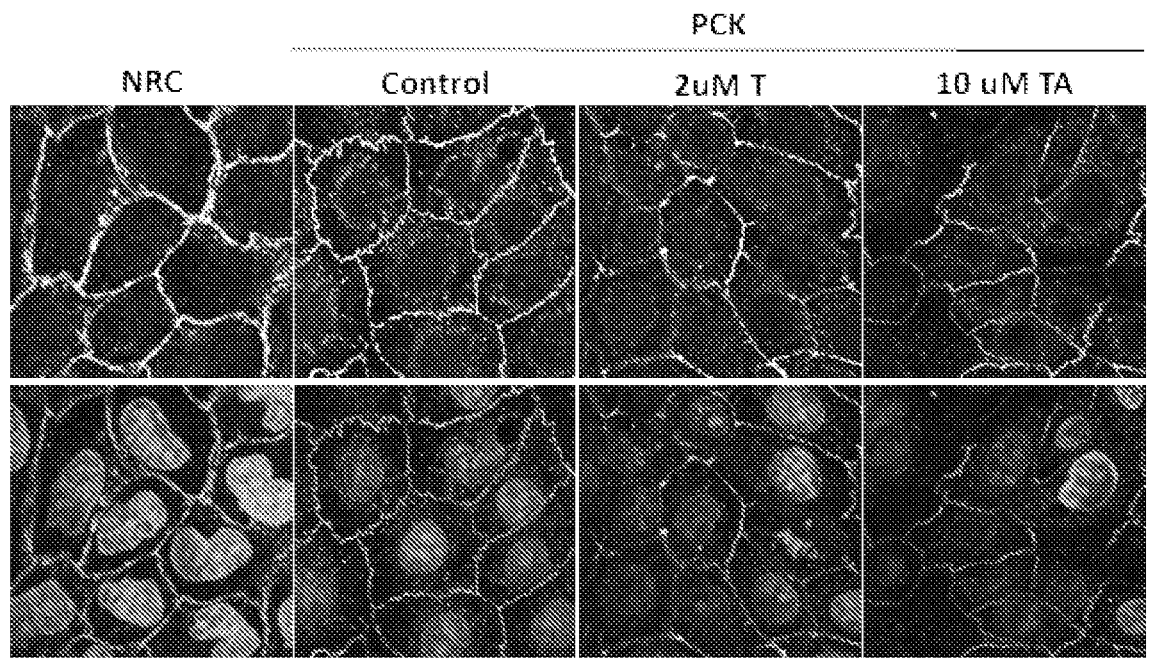
FIG. 6A shows PCK cholangiocytes treated with the HDAC6-specific inhibitor compound A-1 and β-catenin expression analyzed by immunofluorescence and compared to normal cells (NRC).
Figure 6B:
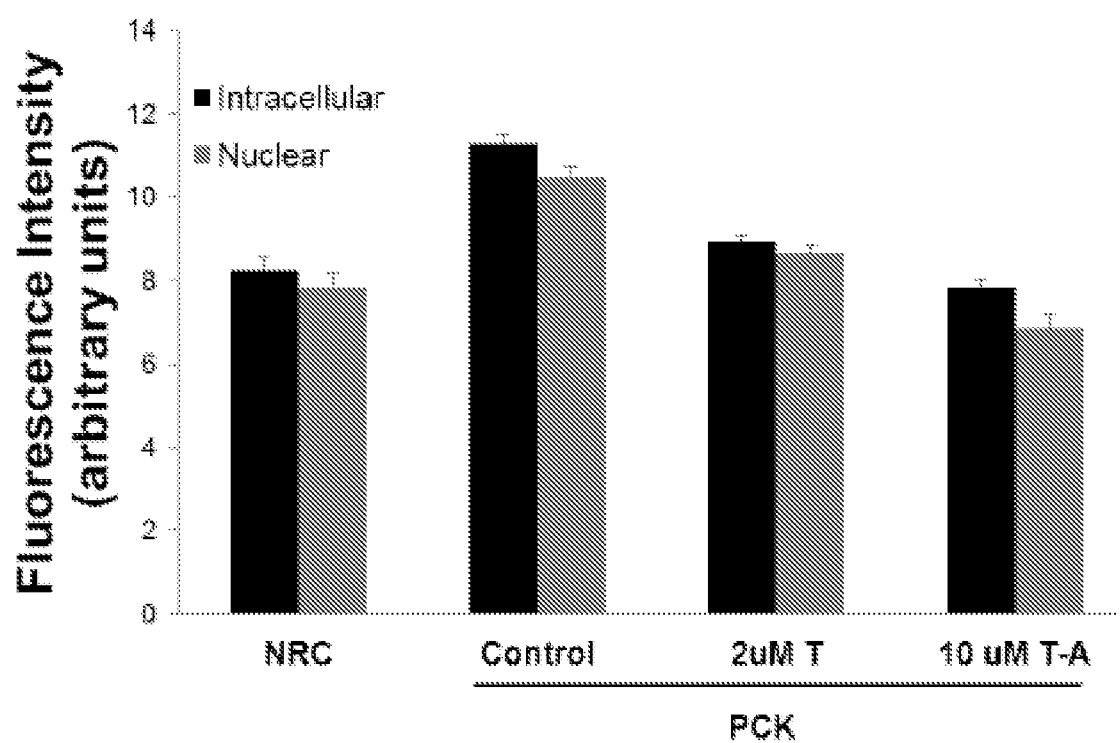
FIG. 6B depicts a β-catenin fluorescence quantification assessment that shows an increased β-catenin expression in PCK cells both in nucleus and cytoplasm compared to NRC. The treatment with the HDAC6-specific inhibitor compound A-1 reduced β-catenin expression in PCK cells.

Furthermore, immunofluorescence analysis of b-catenin subcellular localization also demonstrated that HDAC6 treatment decreased b-catenin expression both in nuclei and cytoplasm (FIG. 6). Consistent with β-catenin reduction, HDAC6 inhibition also caused a decrease in the β-catenin gene target products, cyclin D1 and c-myc, while the levels of acetylated histone H3 remained unaffected (FIG. 3A).

Figure 3B:
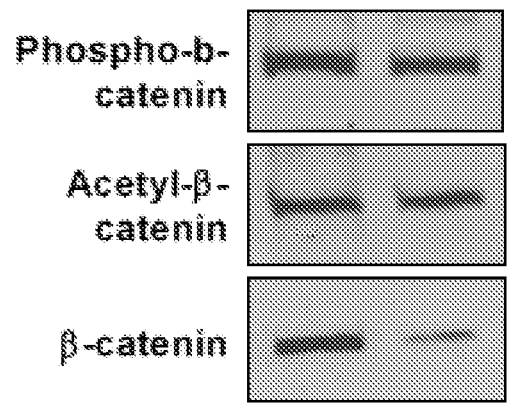
Figure 3C:
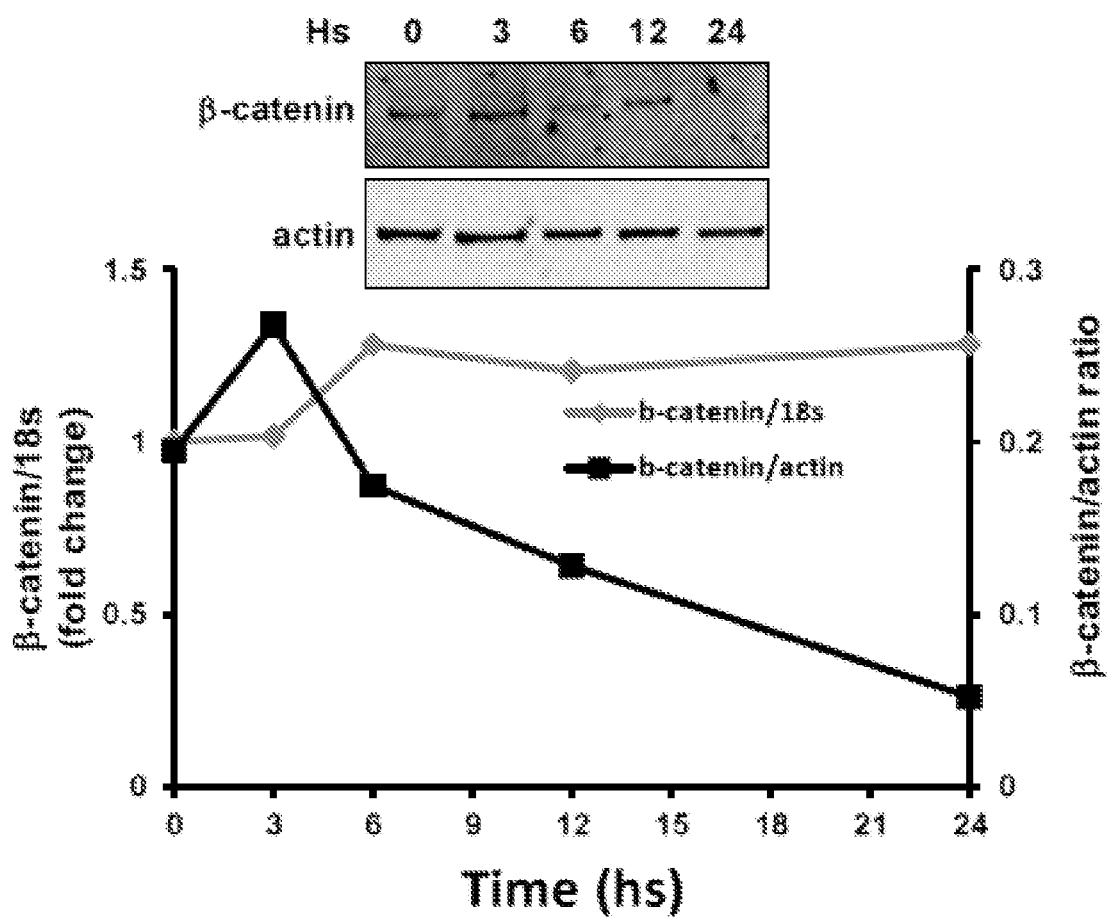

HDAC6 inhibition also increased β-catenin acetylation and phosphorylation (FIG. 3B), consistent with b-catenin destabilization and targeting to degradation. β-catenin protein decreases over time when cells were treated with the HDAC6 inhibitor, while the levels of β-catenin messenger RNA remain stable, suggesting that HDAC6 inhibition induces the degradation of β-catenin protein (FIG. 3C).

Example 6: The Specific HADC6 Inhibitor, Compound A-1, Decreases Cyst Formation In Vivo Rat Pld Model.

The PCK rat model was used because the genetic mutation in this animal is orthologous to that found in human ARPKD. These animals express many of the characteristics of human ADPKD (Lager D J, et al., Kidney Internat 59: 126-136, 2001; Harris, Curr Opin Nephrol Hypertens 11:309-314, 2002). The animals carrying this mutation present with both kidney and liver fibrocystic disease and these animals live long enough to facilitate long-term treatment protocols (Gattone V. H., et al., Nat Med (2003) 9: 1323-1326; Tones V. E., et al., Nat Med (2004) 10:363-364; Masyuk T. V., et al., Gastroenterology (2007) 132:1104-1116, 2007. Female animals show more severe liver disease than male animals.

Figure 4A:
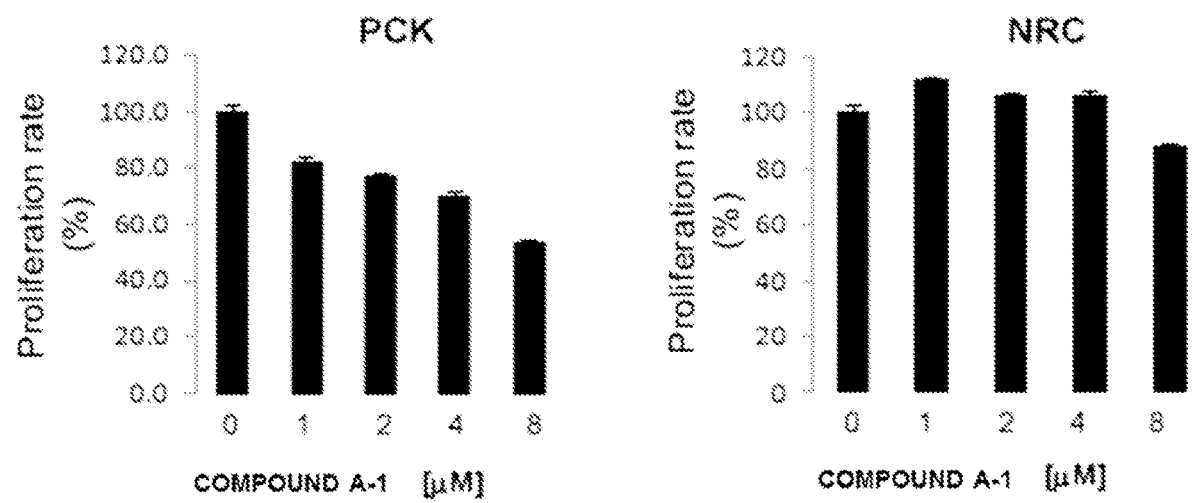
FIGS. 4A-4C shows that the HDAC6 inhibitor, Compound A-1, inhibits cyst growth in vivo.

Normal and PCK cholangiocytes were treated with the HDAC6 specific inhibitor, Compound A-1. PCK cells proliferation was inhibited by the Compound A-1 in a dose dependent manner, and had no significant effect on the proliferation of normal cells (FIG. 4A).

Figure 4B:
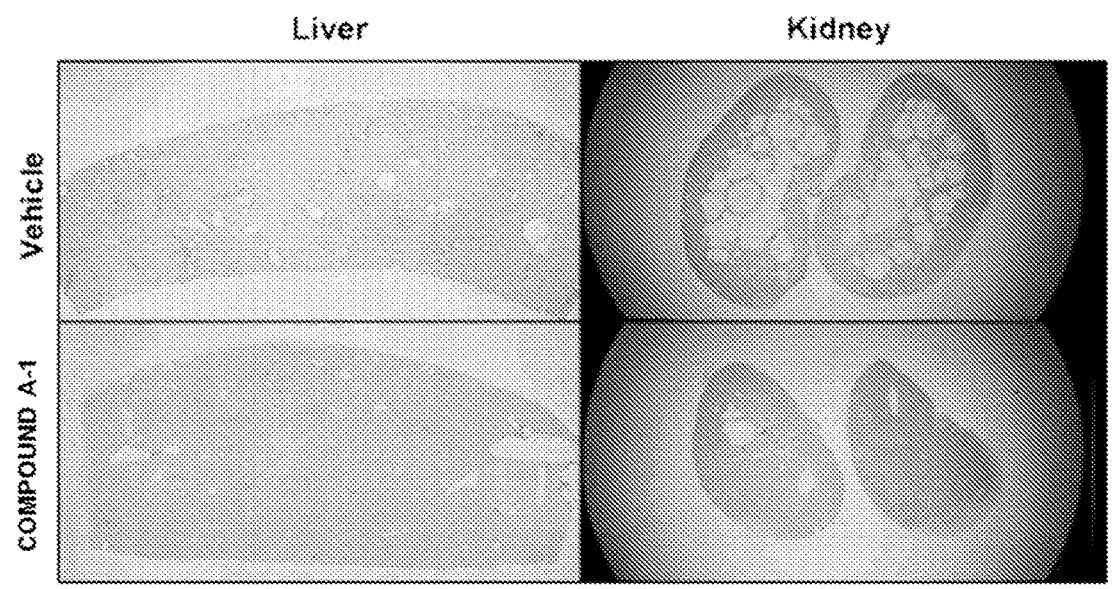
Figure 4C:
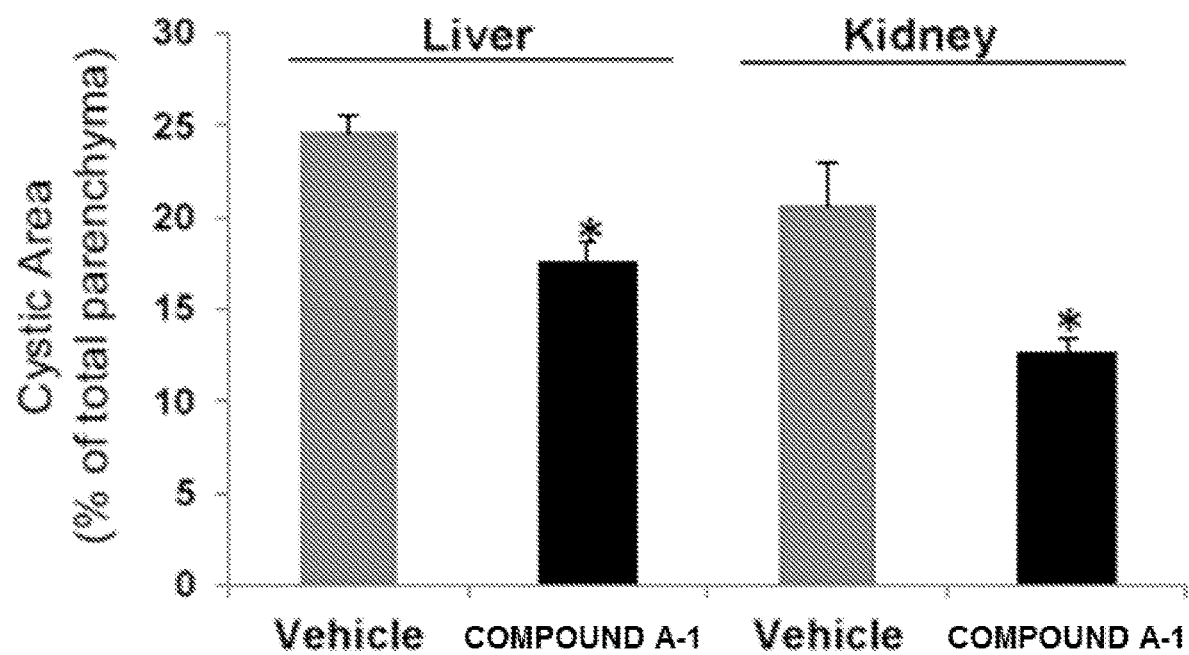

The efficacy of the Compound A-1 was then tested in a PCK rat, an animal model of polycystic liver disease. Both liver and kidney cyst area were significantly reduced by the treatment with the Compound A-1 [by 28.4% and 39.0%, respectively (see FIGS. 4B and 4C). Importantly, liver fibrosis was also reduced by 30.5% (p<0.001).

Figure 7:
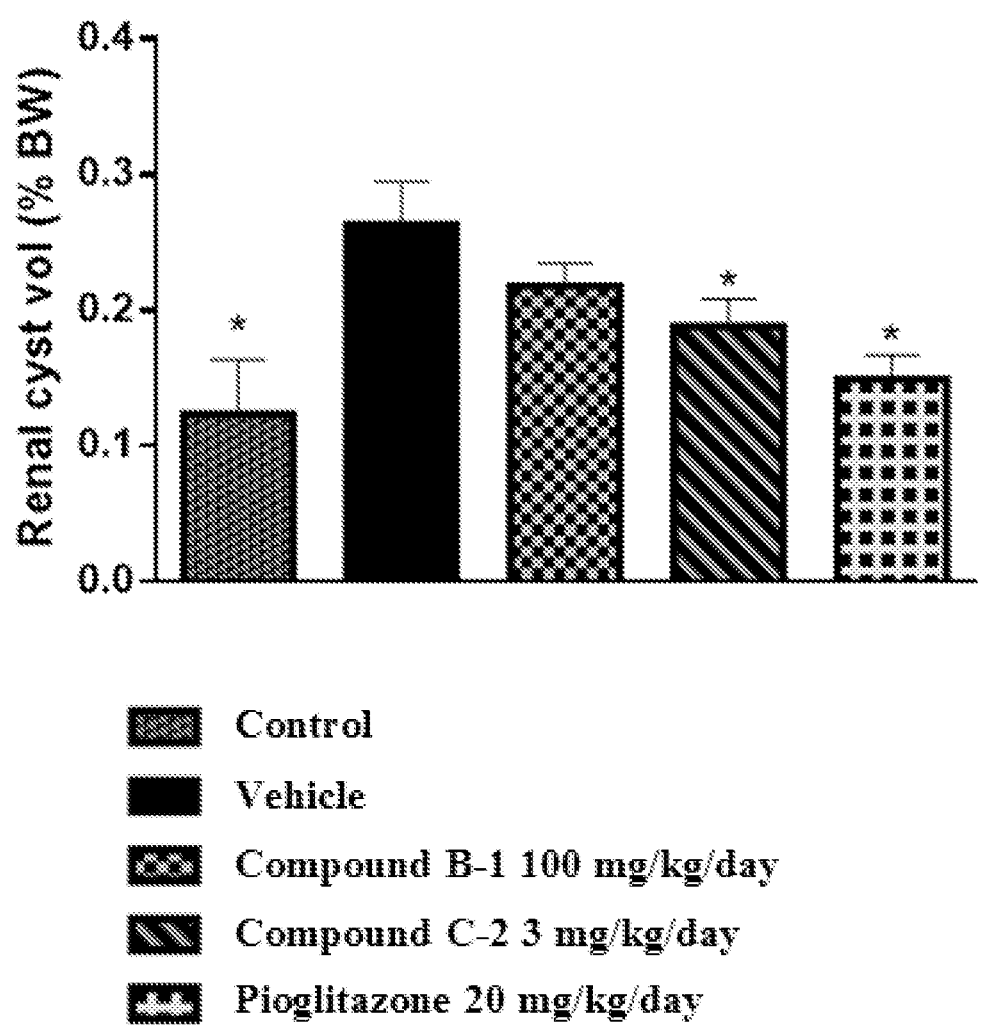
FIG. 7 shows the volume of cysts in the kidneys of male PCK-1 rats treated with HDAC6 inhibitors of Formula I (compound B-1) and Formula II (Compound C-2)

Example 7: The Specific HDAC6 Inhibitor of Compounds B-1 and C-2 Decrease Cyst Formation In Vivo Male PKC-1 rats (4 weeks old, n=12) were treated by oral gavage once daily with the indicated dose of compounds for 12 weeks. The animals were sacrificed and kidneys were removed and fixed in formalin. The volume of cysts in the kidneys was measured by histological analysis (see FIG. 7). As a comparison, 6 rats were sacrificed at 4 weeks to measure the starting volume of renal cysts (control).

The results show that the HDAC6-specific inhibitor compounds B-1 and C-2 decrease cyst formation in vivo.

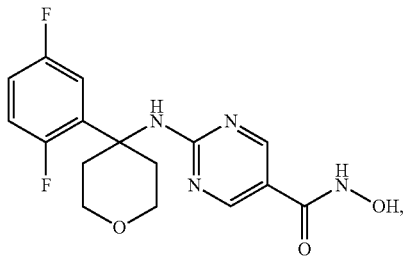
(B-2)

The invention claimed is:

1. A method for treating a polycystic disease comprising:
administering to a subject with a polycystic disease a therapeutically effective amount of a histone deacetylase 6 (HDAC6) specific inhibitor compound selected from the group consisting of:

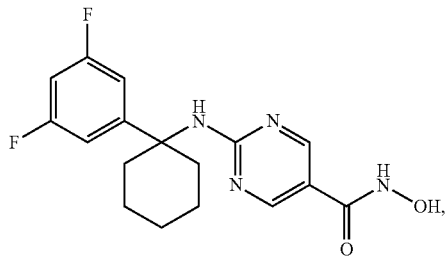
(A-2)

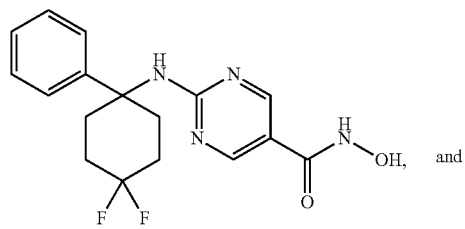
(C-2) and

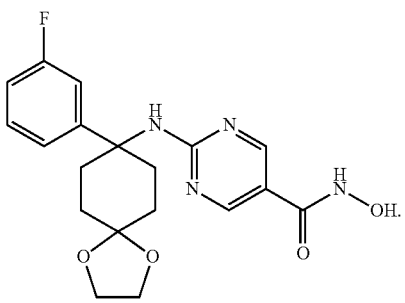

(D-2)

2. The method for treating polycystic disease according to claim 1, wherein the amount of the histone deacetylase 6 (HDAC6) specific inhibitor compound is effective at reducing cyst growth in the subject.

3. The method for treating polycystic disease according to claim 1, wherein the polycystic disease is polycystic liver disease.

4. The method for treating polycystic disease according to claim 2, wherein the cysts are located in the liver.

5. The method for treating polycystic disease according to claim 1, wherein the polycystic disease is renal cystic disease.

6. The method for treating polycystic disease according to claim 5, wherein the renal cystic disease is polycystic kidney disease.

7. The method for treating polycystic disease according to claim 2, wherein the cysts are located in the kidney.

8. The method for treating a polycystic disease according to claim 5, wherein the renal cystic disease is an autosomal dominant polycystic kidney disease (ADPKD).

9. The method for treating a polycystic disease according to claim 5, wherein the renal cystic disease is autosomal recessive polycystic kidney disease (ARPKD).

10. The method for treating a polycystic disease according to claim 1, wherein the amount of the histone deacetylase 6 (HDAC6) specific inhibitor compound is effective at preventing the formation of cysts.

11. The method for treating a polycystic disease according to claim 1, wherein the amount of the histone deacetylase 6 (HDAC6) specific inhibitor compound is effective at inhibiting cholangiocyte proliferation.

12. The method for treating a polycystic disease according to claim 1, wherein the amount of the histone deacetylase 6 (HDAC6) specific inhibitor compound is effective at increasing the amount of bile duct acetylated tubulin.

13. The method for treating a polycystic disease according to claim 1, wherein the amount of the histone deacetylase 6 (HDAC6) specific inhibitor compound is effective at reducing bile duct β-catenin synthesis.

14. The method for treating a polycystic disease according to claim 1, wherein the amount of the histone deacetylase 6 (HDAC6) specific inhibitor compound is effective at increasing bile duct β-catenin phosphorylation and/or acetylation.

15. The method for treating a polycystic disease according to claim 1, wherein the histone deacetylase 6 (HDAC6) specific inhibitor compound II is:

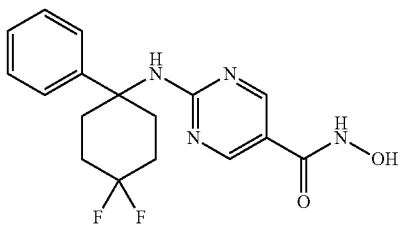 [SMILES: O=C(NO)c1cnc(NC2(c3ccccc3)CCC(F)(F)CC2)nc1]

or a pharmaceutically acceptable salt thereof.

16. The method for treating a polycystic liver disease according to claim 15, wherein the amount of the histone deacetylase 6 (HDAC6) specific inhibitor compound is effective at reducing cyst growth in the subject.

17. The method for treating a polycystic disease according to claim 15, wherein the amount of the histone deacetylase 6 (HDAC6) specific inhibitor compound is effective at inhibiting cholangiocyte proliferation.

* * * * *